(12) United States Patent
Chiosis et al.

(10) Patent No.: US 6,734,165 B2
(45) Date of Patent: May 11, 2004

(54) METHOD FOR RE-SENSITIZING VANCOMYCIN RESISTANT BACTERIA WHICH SELECTIVELY CLEAVE A CELL WALL DEPSIPEPTIDE

(75) Inventors: Gabriela Chiosis, New York, NY (US); Ivo G. Boneca, Vitry sur Seine (FR); W. Clark Still, New York, NY (US)

(73) Assignees: The Trustees of Columbia University in the City of New York, New York, NY (US); The Rockefeller University, New York, NY (US)

( * ) Notice: Subject to any disclaimer, the term of this patent is extended or adjusted under 35 U.S.C. 154(b) by 0 days.

(21) Appl. No.: 09/938,746

(22) Filed: Aug. 23, 2001

(65) Prior Publication Data

US 2003/0125372 A1 Jul. 3, 2003

(51) Int. Cl.[7] .................. A61K 38/16; A61K 38/00; A61K 31/40
(52) U.S. Cl. .................. 514/8; 514/9; 514/11; 514/12; 514/408
(58) Field of Search .................. 514/8, 9, 11, 12, 514/408

(56) References Cited

U.S. PATENT DOCUMENTS

| | | | | |
|---|---|---|---|---|
| 3,067,099 A | * | 12/1962 | McCormick et al. | 167/65 |
| 4,322,343 A | | 3/1982 | Debono | |
| 4,946,941 A | | 8/1990 | Kondo et al. | |
| 5,187,082 A | | 2/1993 | Hamill et al. | |
| 5,312,738 A | | 5/1994 | Hamill et al. | |
| 6,037,447 A | * | 3/2000 | Stack et al. | 530/322 |
| 6,180,604 B1 | * | 1/2001 | Fraser et al. | 514/12 |

FOREIGN PATENT DOCUMENTS

WO     WO 9106566     5/1991

OTHER PUBLICATIONS

Abraham, E.P. and E. Chain, An Enzyme from Bacteria able to Destroy Penicillin, *Nature* 146, 837 (1940).
Perl, T. M., The Threat of Vancomycin Resistance, *Am. J. Med.* 106:5A, 26S–37S (1999).
Wright, G. D. and C. T. Walsh, D–Alanyl–D–alanine Ligases and the Molecular Mechanism of Vancomycin Resistance, *Acc. Chem. Res.* 25, 468–473 (1992).
Walsh, C. T., Vancomycin Resistance: Decoding the Molecular Logic, *Science* 261, 308–309 (1993).
Silva, J.C. et al., In vivo characterization of the type A and B vancomycin resistant enterocossi (VRE) VanRS two–component systems in *Escherichia coli*: A nonpathogenic model for studying the VRE signal trasduction pathways, *Proc. Natl. Acad. Sci. U.S.A.* 95 11951–11956.(1998).
Arthur, M. et al., Structural relationship between the vancomycin resistance protein VanH and 2–hydroxycarboxylic acid dehydrogenases, *Gene* 103, 133–134 (1991).
Bugg, T. D. et al., Molecular Basis for Vancomycin Resistance in *Enterococcus feacium* BM4147:Biosynthesis of a Dispeptide Peptidoglycan Precursor by Vancomycin Resistance Proteins VanH and VanA, *Biochem.* 30, 10408–10415 (1991).
Wu, Z. and C. T. Walsh, Phosphate analogs of D–,D–dipeptides: Slow–binding inhibition and proteolysis protection of VanX, a D–, D–dipeptidase required for vancomycin resistance in *Enterococcus faecium*, *Proc. Natl. Acad. Sci. U.S.A.* 92, 11603–11607 (1995).
Xu, R. et al., Combinatorial Library Approach for the Identification of Synthetic Receptors Targeting Vancomycin–Resistant Bacteria, *J. Am. Chem. Soc.* 121, 4898 (1999).
Ge, M. et al., Vancomycin Derivatives That Inhibit Peptidoglycan Biosynthesis Without Binding D–Ala–D–Ala, *Science* 284, 507–511 (1999).
Sundram, U. N. et al., Novel Vancomycin Dimers with Activity against Vancomycin–Resistant Enterococci, *J. Am. Chem. Soc.* 118, 13107–13108 (1996).
Ohlmeyer M. H. J. et al., Complex synthetic chemical libraries indexed with molecular tags, *Proc. Natl. Acad. Sci. U.S.A.* 90, 10922–10926 (1993).
Templin, M. F. et al., A defect in cell wall recycling triggers autolysis during the stationary growth phase of *Escherichia coli*, *EMBO J.*, 18, 4108–4177 (1999).
Ulijasz, A. T. et al., A Vancomycin–Inducible LacZ Reporter System in *Bacillus subtilis*: Induction by Antibiotics That Inhibit Cell Wall Synthesis and by Lysozyme, *J. Bacteriol.* 178, 6305–6309 (1996).
Baptista, M. et al., Specificity of Induction of Glycopeptide Resistance Genes in *Enterococcus faecalis*, *Antimicrob. Agents Chemother.* 40, 2291–2295 (1996).
Cheng, Y. et al., Sequence–Selective Peptide Binding with a Peptido–A,B–trans–steroidal Receptor Selected from an Encoded Combinatorial Receptor Library, *J. Am. Chem. Soc.* 118, 1813–1814 (1996).
Burger, M., and W.C. Still, Synthetic Ionophores. Encoded Combinatorial Libraries of Cyclen–based Receptors for $Cu^{2+}$ and $Co^{2+}$, *J. Org. Chem.*, 60, 7382–7383 (1995).
Borchardt, A., and W.C. Still, Synthetic Receptor Binding Elucidated with an Encoded Combinatorial Library, *J. Am. Chem. Soc.* 116, 373–374 (1994).
Nelson, R.R., Intrinsically Vancomycin Resistant Gram–positive Organisms: Clinical Relevance and Implications for Infection Control, *Journal of Hospital Infection*, 42, 275–282 (1999).

(List continued on next page.)

*Primary Examiner*—Kevin E. Weddington
(74) *Attorney, Agent, or Firm*—John P. White; Cooper & Dunham LLP

(57) ABSTRACT

The present invention relates a method for re-sensitizing vancomycin resistant Gram-positive bacteria in which resistance results from the conversion of an amide bond to an ester bond in the cell wall peptide precursors of the bacteria which comprises using an antibacterial amount of vancomycin or a homolog of vancomycin and an amount of an agent effective to selectively cleave the ester bond so as to thereby re-sensitize vancomycin resistant bacteria.

73 Claims, 21 Drawing Sheets

OTHER PUBLICATIONS

T.G. Emori, and R. P. Gaynes, An Overview of Nosocomial Infections, Including the Role of the Microbiology Laboratory, *Clin Microbiol. Rev.*, 6(4):428–442 (1993).

N. Woodford, Glycopeptide–resistant enterococci: a decade of experience, *J. Med. Microbiol.* 47:849–862 (1998).

G. L. French, Enterococci and Vancomycin Resistance, *Clin. Infect. Dis.*, Suppl 1:S75–S83 (1998).

C.T. Walsh, Vancomycin Resistance: Decoding the Molecular Logic, *Science*, 261:308–309 (1993).

G.D. Wright et al., Characterization of VanY, a DD–Carboxypeptidase from Vancomycin–Resistant *Enterococcus faecium* BM4147, *Antimicrob. Agents. Chemother.*, 36(7):1514–1518 (1992).

P.E. Reynolds et al., Glycopeptide resistance mediated by enterococcal transposon Tn 1546 requires production of VanX for hydrolysis of D–alanyl–D–alanine, *Mol. Microbiol.*, 13(6):1065–1070 (1994).

H. P. Netsler et al., A General Method for Molecular Tagging of Encoded Combinatorial Chemistry Libraries, *J. Org. Chem.*, 59:4723–4724 (1994).

S. Handwerger et al., Vancomycin Resistance Is Encoded on a Pheromone Response Plasmid in *Entercoccus faecium* 228, *Antimicrob. Agents. Chemother.*, 34:358–360 (1990).

A. E. Jacobs and S. J. Hobbs, Conjugal Transfer of Plasmid–Borne Multiple Antibiotic Resistance in *Streptococcus faecalis var. zymogenes*, *J. Bacteriol.*, 117(2):360–372 (1974).

M. H. Lai and D. R. Kirsch, Induction Signals for Vancomycin Resistance Encoded by the vanA Gene Cluster in *Enterococcus faecium*, *Antimicrob. Agents. Chemother.*, 40(7):1645–1648 (1996).

B.L.M. De Jonge et al., Peptidoglycan Composition of Vancomycin–Resistant *Enterococcus faecium*, *Microb. Drug Resist*. 2:225–229 (1996).

S. Evers et al., Genetics of Glycopeptide Resistance in *Enterococci*, *Microb. Drug Resist*. 2:219–223 (1996).

P.E. Reynolds, Biochemistry, and Mechanism of Action of Glycopeptide Antibiotics, *Eur. J. Microbiol. Infect. Dis.* 8:943–950 (1993).

K. Matusmoto, A Vancomycin–Related Antibiotic From Steptomyces Sp. K–288, *J. Antibiotics, Ser. A.* 14(3):141–146.

* cited by examiner

METHOD FOR RE-SENSITIZING VANCOMYCIN RESISTANT BACTERIA WHICH SELECTIVELY CLEAVE A CELL WALL DEPSIPEPTIDE

The invention disclosed herein was made with Government support under NIH Grant No. 5-R01-HL-25634-18 from the National Institutes of Health. Accordingly, the U.S. Government has certain rights in this invention.

Throughout this application, various references are identified by citations or a number in parenthesis, in which case their full citations appear on the pages following the Detailed Description immediately preceding the claims. Disclosure of these references in their entireties are hereby incorporated by reference into this application to more fully describe the state of the art to which this invention pertains.

FIELD OF THE INVENTION

The present invention relates to a method for re-sensitizing vancomycin resistant Gram-positive bacteria in which resistance results from the conversion of an amide bond to an ester bond in the cell wall peptide precursors of the bacteria which comprises using an antibacterial amount of vancomycin or a homolog of vancomycin and an amount of an agent effective to selectively cleave the ester bond so as to thereby re-sensitize vancomycin resistant bacteria.

BACKGROUND OF THE INVENTION

The introduction of the first antimicrobial agents allowed physicians and patients to manage infectious diseases effectively. Unfortunately, even before penicillin was introduced commercially, researchers had identified the first resistant *Staphylococcus aureus* (1). Since then, many new antimicrobials have been developed to combat the emergence of resistance. These advances increased the confidence that infectious diseases are non-fatal and still manageable. Nevertheless, with the medical progresses that allow people to live longer and the boost of various debilitating immune conditions (AIDS, cancer, organ transplants), a new human population emerged as being at great risk of infectious diseases caused in majority by two common nosocomial pathogens, Staphylococcus and Enterococcus species (2). The incidence of staphylococcal strains resistant to virtually all the antimicrobial agents except vancomycin has increased drastically during the last decade. Additionally, enterococcal infections are becoming increasingly resistant even to vancomycin, raising the alarming possibility that resistance genes will eventually be transmitted to staphylococci (3–5). One of the greatest concerns with vancomycin resistant enterococci (VRE) is that the resistance to vancomycin will be picked up by *Staphylococcus aureus* through genetic recombination. Many forms of *S. aureus* have already become resistant to methicillin and can now only be treated with vancomycin. There is significant concern that if *S. aureus* also becomes resistant to vancomycin, the health care profession will be left without treatment for these types of infections. Increasing resistance among several types of Gram-positive bacteria associated with common and potentially life-threatening infections complicate the treatment of serious infections and has been linked to extended hospitalizations, higher medical costs and high mortality rates.

Like the family of β-lactam antibiotics, vancomycin acts on peptidoglycan metabolism. The peptidoglycan is essential for bacterial survival because of its function as the exoskeleton that prevents cell rupture due to internal pressure. By binding to the D—Ala—D—Ala moiety of the bacterial cell wall precursors, vancomycin interferes with the growth of the peptidoglycan (6). In the resistant strains with vanA or vanB phenotype however, some of the D—Ala—D—Ala moiety of the cell wall precursors is substituted by analogous D—Ala—D—Lac ones (7–9). Only a small percentage of the enterococcus peptidoglycan layer is needed to be structurally altered from D—Ala—D—Ala to D—Ala—D—Lac to cause an increase in the vancomycin MIC (10% of the altered peptidoglycan increases the MIC of vancomycin from 2 to 32 ug/ml).

Resistant bacteria carry a transportable element encoding nine genes that contribute to the resistance phenotype (10). These gene products include VanS, a transmembrane protein that senses directly or indirectly the presence of vancomycin. Once autophosphorylated, VanS transmits a signal to a response regulatory protein VanR that activates transcription of the other resistance genes (11). VanA is involved in the synthesis of the depsipeptide D—Ala—D—Lac while VanH converts pyruvate into D-lactate. This pathway is essential for the resistance phenotype (12,13). VanX is a $Zn^{2+}$ dependent pepsidase that selectively cleaves D—Ala—D—Ala leading to an accumulation of the depsipeptide, and thus, of precursors with altered D—Ala—D—Lac termini (14,15). VanY is a membrane bound D—D-carboxypeptidase that hydrolyses the normal cell wall precursor lipid-intermediates, further increasing the pool of precursors with altered termini (16). However, the formation of D—Ala—D—Ala continues in the cell due to the activity of the native enterococcal D—Ala—D—Ala ligase. Because vancomycin binds to D—Ala—D—Ala substrates, a mechanism is required to prevent D—Ala—D—Ala from being incorporated into the cell wall. VanX and vanY perform this function. As a result of the incorporation of D—Ala—D—Lac by vancomycin resistant enterococcus (VRE), the affinity of vancomycin for the peptidoglycan layer diminishes over 1000-fold, leading to antibiotic resistance. VanA strain is the most common phenotype of VRE and is described by inducible, high-level resistance that is associated with the van genes that lead to D—Ala—D—Lac altered termini.

In order to bypass resistance, vancomycin has been modified to enhance its binding to D—Ala—D—Lac and inhibitors of the D—Ala—D—Lac biosynthetic pathway have been sought (17–19). Here we propose another approach—the selective and catalytic cleavage of the D—Ala—D—Lac depsipeptide by small molecules. By reducing the concentration of precursors with altered termini one would expect to re-sensitize the bacteria to vancomycin. A small molecule that performs such task could be used in concert with vancomycin (or vancomycin derivatives with higher affinity) in the treatment of vanA resistant strains.

SUMMARY OF THE INVENTION

One of the most challenging situations for the immunocompromised patients is the development of vancomycin-resistant enterococci (VRE), an increasingly frequent cause of hospital-acquired infections in the United States. These organisms are resistant to virtually all currently available antibiotics including vancomycin, considered the agent of last resort for Gram-positive infections. VanA strain is the most common phenotype of VRE and is described by inducible, high-level resistance that is associated with the van genes that lead to D—Ala—D—Lac cell wall altered termini. Here we describe the development of small molecules that catalytically and selectively cleave the altered termini of the bacteria cell wall so as to disable the antibiotic-resistance mechanism in these pathogens. The molecules re-sensitize bacteria to the drug and could be used in concert with vancomycin in the treatment of VRE.

The invention provides a method of treating a subject afflicted with an infection caused by glycopeptide antibiotic resistant Gram-positive bacteria, such as vancomycin resistant Gram-positive bacteria, in which resistance results from the conversion of an amide bond to an ester bond in the cell wall peptide precursors of the bacteria which comprises administering to the subject an antibacterial amount of glycopeptide antibiotic, such as vancomycin or a homolog of vancomycin, and an amount of an agent effective to selectively cleave the ester bond so as to thereby treat the subject.

The invention also provides a method of killing glycopeptide antibiotic resistant Gram-positive bacteria, such as vancomycin resistant Van A, Van B, Van D, or Van G Gram-positive bacteria which comprises contacting the bacteria with an agent that selectively cleaves D—Ala—D—Lac cell wall depsipeptides in the bacteria in an amount effective to cleave such depsipeptides and an antibacterial amount of glycopeptide antibiotic, such as vancomycin or a homolog of vancomycin, so as to thereby kill the bacteria.

The invention further provides a method for determining whether a test compound selectively cleaves an ester bond present between two amino acid-like moieties in a depsipeptide which comprises contacting a compound comprising the structure X-Y, wherein each of X and Y are amino acid-like moieties and — is an ester bond with the test compound and determining whether the test compound cleaves the ester bond.

In another aspect, the invention provides a method of treating a subject afflicted with an infection caused by glycopeptide antibiotic resistant Gram-positive bacteria in which resistance results from the conversion of an amide bond to an ester bond in the cell wall peptide precursors of the bacteria which comprises administering to the subject an antibacterial amount of a glycopeptide antibiotic and an amount of an agent effective to selectively cleave said ester bond so as to thereby treat the subject.

In addition, the present invention also provides a method of killing glycopeptide antibiotic resistant Gram-positive bacteria which comprises contacting the bacteria with an agent that selectively cleaves D—Ala—D—Lac cell wall depsipeptides in the bacteria in an amount effective to cleave such depsipeptides and an antibacterial amount of the glycopeptide antibiotic so as to thereby kill the bacteria.

DETAILED DESCRIPTION OF THE INVENTION

Figure 1:
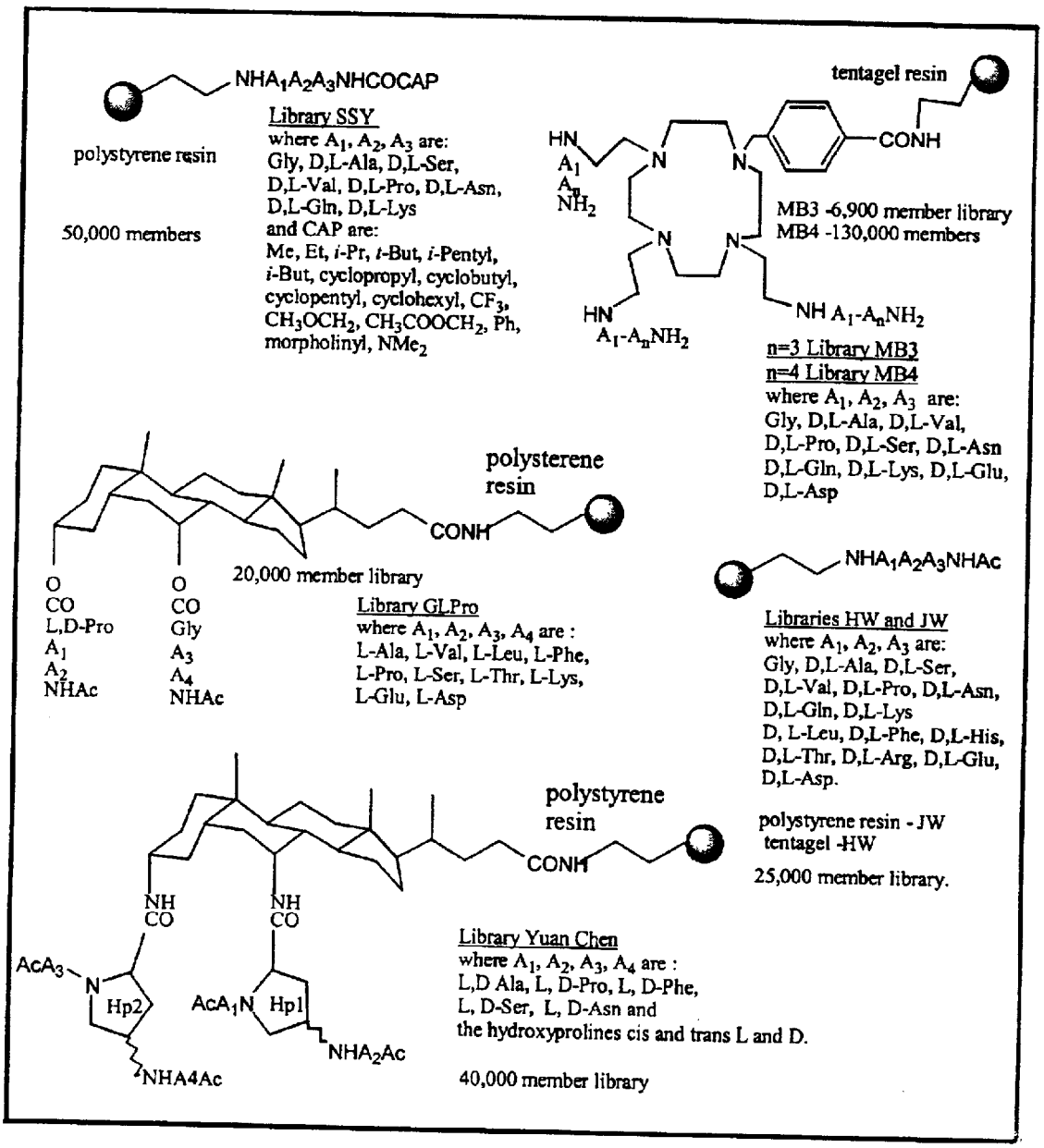
FIG. 1. Combinatorial libraries selected to screen for cleavage of D—Ala—D—Lac.

This invention provides a method of treating a subject afflicted with an infection caused by glycopeptide antibiotic resistant Gram-positive bacteria, such as vancomycin resistant Gram-positive bacteria, in which resistance results from the conversion of an amide bond to an ester bond in the cell wall peptide precursors of the bacteria which comprises administering to the subject an antibacterial amount of vancomycin or a homolog of vancomycin and an amount of an agent effective to selectively cleave the ester bond so as to thereby treat the subject.

In one embodiment of the invention, the subject is a human being.

In general, the agent is an activated nucleophile and is further characterized by the presence within the agent of an electrophile and chirality complementary to a bacterial cell wall depsipeptide.

In one embodiment of the invention, the agent is represented by the formula S—Pro—$C_n$.

In another embodiment of the invention, the agent has the structure:

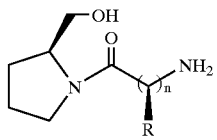

wherein n is an integer from 1 to 6 inclusive and R is hydrogen or a $C_1$ to $C_6$ straight chain or branched alkyl group.

Preferably, the agent catalytically cleaves the ester bond in the cell wall peptide precursors, for example, the ester bond in the structure D—Ala—D—Lac.

The agent may be administered prior to administering a glycopeptide antibiotic, such as vancomycin or the homolog of vancomycin. Specifically, the agent is administered a sufficient period of time prior to administering vancomycin or the homolog of vancomycin to permit cleavage of the ester bond in the cell wall peptide precursors to be effected.

Alternatively, the agent and glycopeptide antibiotic, such as vancomycin or the homolog of vancomycin are administered simultaneously, for example, the agent may be covalently attached to vancomycin or the homolog of vancomycin.

In the practice of the invention, the bacteria are typically Van A, Van B, Van D or Van G Gram positive bacteria.

In another preferred embodiment of the invention, the bacteria may be Staphylococcus bacteria, S. aureus bacteria, Enterococcus bacteria, Streptococcus bacteria, Leuconostoc bacteria, Pediococcus bacteria, Lactobacillus bacteria, and Erysipelothrix bacteria.

This invention also provides a method of killing vancomycin resistant Van A, Van B, Van D, or Van G Gram-positive bacteria which comprises contacting the bacteria with an agent that selectively cleaves D—Ala—D—Lac cell wall depsipeptides in the bacteria in an amount effective to cleave such depsipeptides and an antibacterial amount of vancomycin or a homolog of vancomycin so as to thereby kill the bacteria.

In one embodiment of the invention, the invention provides a method of killing glycopeptide antibiotic resistant Gram-positive bacteria, such as vancomycin resistant Van A, Van B, Van D, or Van G Gram-positive bacteria which comprises contacting the bacteria with an agent that selectively cleaves D—Ala—D—Lac cell wall depsipeptides in the bacteria in an amount effective to cleave such depsipeptides and an antibacterial amount of glycopeptide antibiotic, such as vancomycin or a homolog of vancomycin, so as to thereby kill the bacteria wherein the agent is an activated nucleophile, and the agent is further characterized by the presence within the agent of an electrophile and chirality complementary to the bacterial cell wall depsipeptide.

In another embodiment of the invention, the agent maybe represented by the formula S—Pro—Cn.

In one embodiment of the invention, the invention provides a method of killing glycopeptide antibiotic resistant Gram-positive bacteria, such as vancomycin resistant Van A, Van B, Van D, or Van G Gram-positive bacteria which comprises contacting the bacteria with an agent that selectively cleaves D—Ala—D—Lac cell wall depsipeptides in the bacteria in an amount effective to cleave such depsipeptides and an antibacterial amount of glycopeptide antibiotic, such as vancomycin or a homolog of vancomycin, so as to thereby kill the bacteria, wherein the agent has the structure:

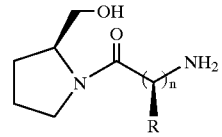

wherein n is an integer from 1 to 6 inclusive and R is hydrogen or a $C_1$ to $C_6$ straight chain or branched alkyl group.

The invention provides a method of killing glycopeptide antibiotic resistant Gram-positive bacteria, such as vancomycin resistant Van A, Van B, Van D, or Van G Gram-positive bacteria which comprises contacting the bacteria with an agent that selectively cleaves D—Ala—D—Lac cell wall depsipeptides in the bacteria in an amount effective to cleave such depsipeptides and an antibacterial amount of glycopeptide antibiotic, such as vancomycin or a homolog of vancomycin, so as to thereby kill the bacteria, where the agent preferably, catalytically cleaves the ester bond in the D—Ala—D—Lac depsipeptide.

In the practice of the invention, the agent is administered prior to administering the glycopeptide antibiotic, such as vancomycin or the homolog of vancomycin, desirably a sufficient period of time prior to administering vancomycin or the homolog of vancomycin to permit cleavage of the ester bond to be effected in the D—Ala—D—Lac depsipeptide.

Alternatively, the agent and the glycopeptide antibiotic, such as vancomycin or the homolog of vancomycin may be administered simultaneously, e.g. the agent may be covalently attached to vancomycin or the homolog of vancomycin.

In yet another embodiment, this invention provides a method for determining whether a test compound selectively cleaves an ester bond present between an amino acid and an α-hydroxy carboxylic acid in a depsipeptide which comprises contacting a compound of the structure X-Y, where X is an amino acid and Y is α-hydroxy carboxylic acid and — is an ester bond, with the test compound and determining whether the test compound cleaves the ester bond.

In yet another embodiment, the invention provides a method for determining whether a test compound selectively cleaves an ester bond present between two amino acid-like moieties in a depsipeptide which comprises contacting a compound comprising the structure X-Y, wherein each of X and Y are amino acid-like moieties and — is an ester bond with the test compound and determining whether the test compound cleaves the ester bond, for example where the ester bond is present in the structure D—Ala—D—Lac.

In an embodiment of invention, the compound comprises the structure L-(X-Y) wherein (X-Y) is D—Ala—D—Lac, and wherein L is a detectable label, for example a dye.

In one embodiment of the invention, the test compound is bound to a solid support.

In yet another embodiment of the invention, the test compound is present in a collection of compounds containing nucleophiles, for example, a combinatorial library of compounds.

As used herein "homolog of vancomycin" refers to vancomycin having at least one more $CH_2$ or alkene group in its molecule than the vancomycin molecule. See for example U.S. Pat. No. 6,037,447, the contents of which are hereby incorporated by reference into this application.

As used herein "glycopeptide antibiotic" refers to a class of compounds disclosed in, by way of example and not as a limitation to the present invention, U.S. Pat. No. 5,977,062, the contents of which are hereby incorporated by reference into this application. For example, glycopeptide antibiotics could include vancomycin as disclosed in U.S. Pat. No. 3,067,099; A82846A, A82846B, and A82846C as disclosed in U.S. Pat. No. 5,312,738; PA-42867 factors A, C, and D as disclosed in U.S. Pat. No. 4,946,941; A83850 as disclosed in U.S. Pat. No. 5,187,082; avoparcin as disclosed in U.S. Pat. No. 4,322,343; actinoidin, also known as K288 (J. Antibiotics Series A 14:141 (1961)); helevecardin (Chem. Abstracts 110:17188 (1989); galacardin (Chem. Abstracts 110:17188 (1989); and M47767 (PCT International Application No. WO 91/06566).

Organisms intrinsically resistant to vancomycin usually produce D—Ala—D—Lac. Theoretically, SProC5 alone could be bactericidal against such bacteria(e.g., Leuconostoc, Pediococcus, Lactobacillus and Erysipelothrix sp.) (34).

The following description and examples are presented to further illustrate and explain the present invention and should not be taken as limiting in any regard. Unless otherwise indicated in the examples and elsewhere in the specification and claims, all parts and percentages are by weight. Temperatures are in degrees Centigrade.

EXPERIMENTAL DETAILS

Combinatorial Library Screening

To find small molecules that cleave the D—Ala—D—Lac depsipeptides, the red dye-labeled analog 1 is prepared as a probe (Scheme 1).

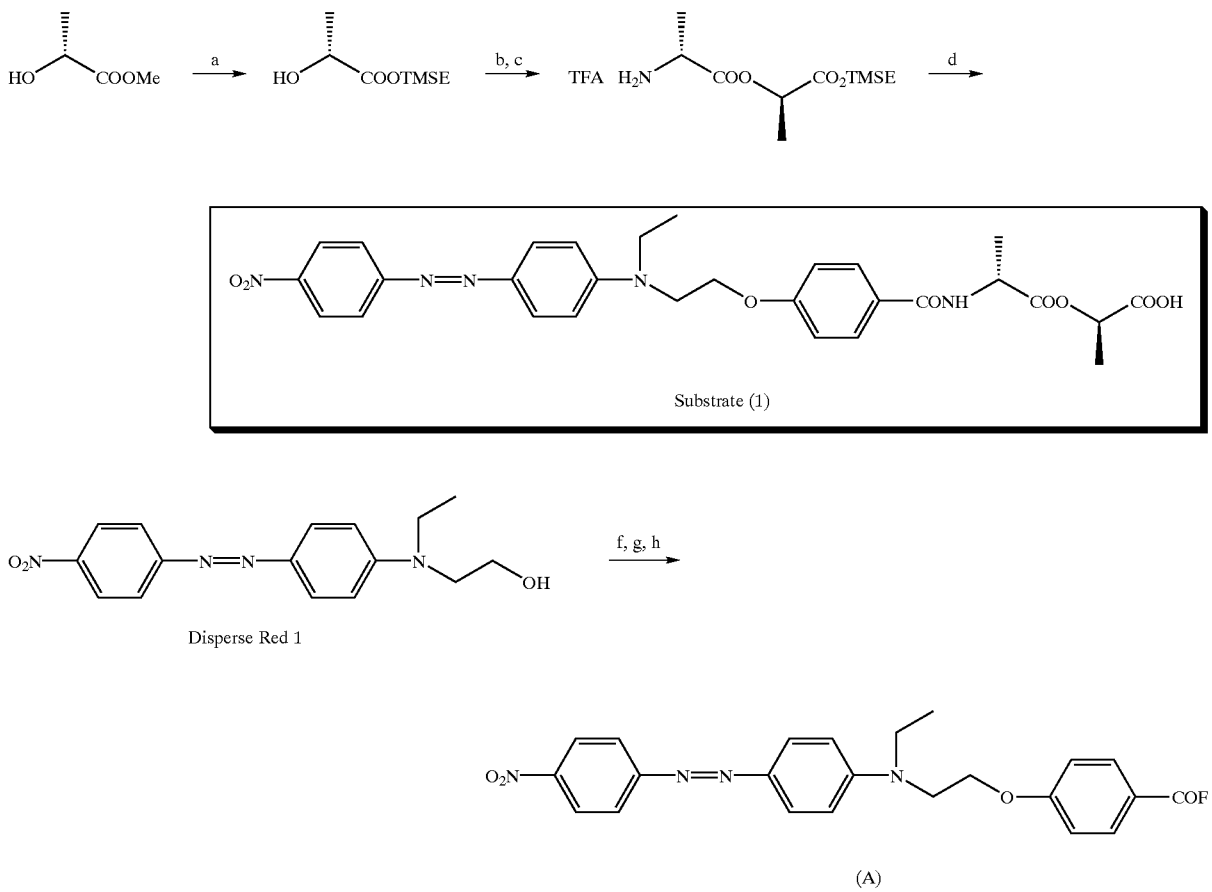

Scheme 1. a. 2-(Trimethylsilyl)ethanol, Ti(i-PrO)$_4$, THF; b. BocD—AlaCOF, DIEA, DMAP, DCM; c. TFA:DCM= 4:1; d. A, DIEA, DMAP, DCM; e. TBAF; f. Methyl 4-hydroxybenzoate, DEAD, PPh$_3$, toluene:DCM=5:1; g. LiOH; h. Cyanuric Fluoride, pyridine, DCM.

Substrate 1 is treated with combinatorial libraries of potential nucleophiles on solid phase synthesis beads (2), and then those library members are selected that covalently linked the dye to a bead (3). This could be possible assuming that noncovalently bound material would be washed away with a polar solvent (Scheme 2).

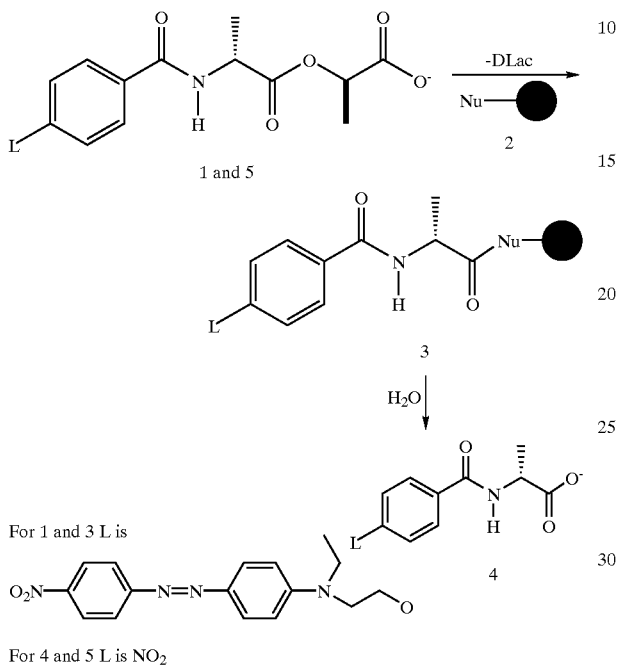

Scheme 2. Strategy for active sequence determination.

The libraries used for screening (i.e., the libraries used in assays were described in: (a) M. Burger, W. C. Still, *J. Org. Chem.* 60, 7382 (1995); (b) A. Borchardt, W. C. Still, *J. Am. Chem. Soc.* 116, 373 (1994). (c) Y. Cheng, T. Suenaga, W. C. Still, *J. Am. Chem. Soc.* 118, 1813 (1996). (d) H. Wenemers, thesis, Columbia University (1996); (e) G. Li, thesis, Columbia University (1993); (f) E. J. Iorio, thesis, Columbia University (1999)), are presented in FIG. 1 and were randomly selected from the Still group archive to achieve higher structural diversity. All libraries posses amino acid building blocks, however, the variance rises from the scaffold that allows a structurally different organization of these building blocks. All peptides were side chain deprotected and washed with DCM/TEA after TFA deprotection to ensure that all possible nucleophiles were in the unprotonated state.

The assay for screening these libraries against 1 involves shaking a desired amount of library beads with the solution of labeled substrate for a period of time. To the library beads were added 200 μL solution of substrate 1 in 12DCE (or DMF), and the mixture was rotated for 3–5 days in a small glass vial. DMF was added and shaking continued for 1 h. Solvent was removed and the washing was repeated several times. One wash was performed with one drop of benzylamine added to DMF to remove any remaining physically bound substrate. The strongly red beads were picked individually in 1.5 μL DMF (in 25 μL capillaries) and photolysed for 6 h under a short wave UV lamp. Decoding was achieved by injecting the content of each capillary in EC-GC and comparing the chromatogram to a standard (20,21).

After the reaction occurred, the label-carrying beads were selected and analyzed (20,21). The initial assays were performed in 1,2-dichloroethane (12DCE) at a concentration of 2.3 mM in substrate 1. Results revealed that in every library the active sequences carried serine at the amino-terminal position. This finding is remarkable considering that other nucleophiles such as Thr, Lys and terminal amino functionality, present in the screened libraries, did not appear at that position in the red beads.

Additionally:

for library GLPro, 80% of the active beads carried the sequence D-Pro—L—Pro—L—Ser on the first arm (C3), while the other 20% Gly—L—Pro—L—Ser on the second arm (C7)

library MB3 showed activity only after previous equilibration with Cu(OAc)$_2$. Position $A_2A_3$ was always occupied by the sequence Pro—Ser, while $A_1$ was somehow variable library MB4 revealed only one active sequence: D—Asn—L—Lys—L—Pro—L—SerNH$_2$ library SSY carried exclusively the dimethylurea capping group from a choice of 14 others, and the most colored beads had frequently Pro and Lys in a neighboring position to the terminal Ser library Yuan Cheng exhibited activity only if initially equilibrated with Cu(OAc)$_2$. Under those conditions, 85% of the active beads had the calibration mark: trans L-hydroxyPro1-$A_1$-$A_2$ cis,trans-L-hydroxyPro2-D-Ser-$A_4$ libraries HW and JW, acetylated tripeptide libraries, although carrying a larger selection of amino acids than SSY, showed no activity under the assay conditions Control assays were performed with side chain protected libraries, and additionally, with the trimethylsilyl ethyl ester of the substrate 1. Neither assay resulted in active sequences.

To improve selectivity in the case of library SSY, assays were performed in different solvents and lower concentrations. From a choice of 12DCE, DCM, THF and DMF, best results were obtained in DMF where selectivity and intensity of the beads were enhanced. A decrease in concentration of the substrate to 0.85 mM also improved selectivity. This concentration proved to be the lower threshold for eye detection of red beads.

Under these conditions, three sequences were most prominently found:

X—L—Lys—L—Ser dimethylurea

X—D—Lys—D—Ser dimethylurea where X was variable and

L—Lys—D—Pro—L—Ser dimethylurea

After a careful analysis of the results, one can speculate that all active sequences carry a nucleophile (Ser) and an electrophile (Lys in most cases, Cu$^{2+}$ for libraries Yuan Chen and MB3, probably a backbone NH for library GLPro). These must be effectively oriented to make the nucleophilic attack of serine possible. The prevalence of Pro suggests that this amino acid may be involved in inducing conformational rigidity and therefore, pre-organization of the active sites.

Computer Modeling of the Active Peptides

Figure 2:
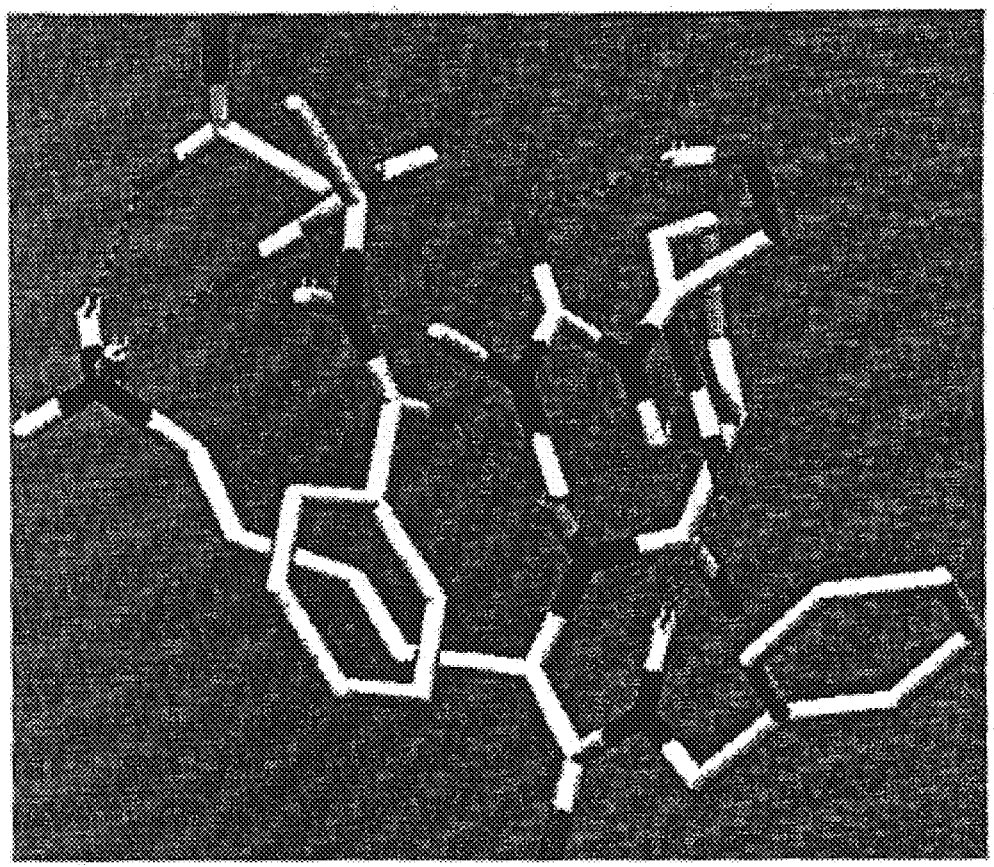
FIG. 2. Computer generated model of the complex of BnNHL-Lys-D-Pro-L-Ser dimethylurea 4a with PhNH—D—Ala—D—Lac. Calculated hydrogen bonds are depicted by dashed lines.

To gain a better understanding of why these sequences were favored and how they work, molecular modeling studies were carried out on selected sequences and on the complexes of these sequences with D—Ala—D—Lac (FIG. 2). Simulations were performed using the GB/SA solvation method for water and AMBER* force field, as implemented in Macromodel V6.0. We used MCMM (Monte Carlo Multiple Minimum) alternated with LMCS (Low Frequency Mode Conformational Search) as conformational search methods. We found that MCMM performed better for finding minima different from the initial conformations, while LMCS for minima close to the initial conformations. Generally, a search was started with MCMM, the output conformations were re-minimized and the conformations lower than 3 or 5 kcal were used as input for a new search using LMCS until convergence was obtained. This method was applied for the sequence BnNHL—Lys—D—Pro—L—Ser dimethylurea (4a), an active sequence from library SSY.

Modeling supports the observations deducted from the combinatorial assays. The structural skeleton permits Lys and Ser to be in close proximity. Lys is involved in binding the carboxylate of D—Ala—D—Lac in addition to its role as the electrophile that stabilizes the tetrahedral transition state. Additionally, the nucleophilicity of Ser is enhanced by hydrogen bonding to the urea capping group. This explains why the dimethyl urea capping group (the best hydrogen acceptor) was the only one that occurred in the active sequences resulted from the library SSY. Furthermore, the hydroxyl is favorably positioned for attacking the ester group of the depsipeptide.

Study of the Electivity and Efficiency of these Peptides in Cleaving D—Ala—D—Lac To test the efficiency of these simple peptides in cleaving D—Ala—D—Lac under physiologically relevant conditions, we chose studying L—Lys—D—Pro—L—Ser dimethylurea, an active sequence found more frequently in the assays.

Figure 3:
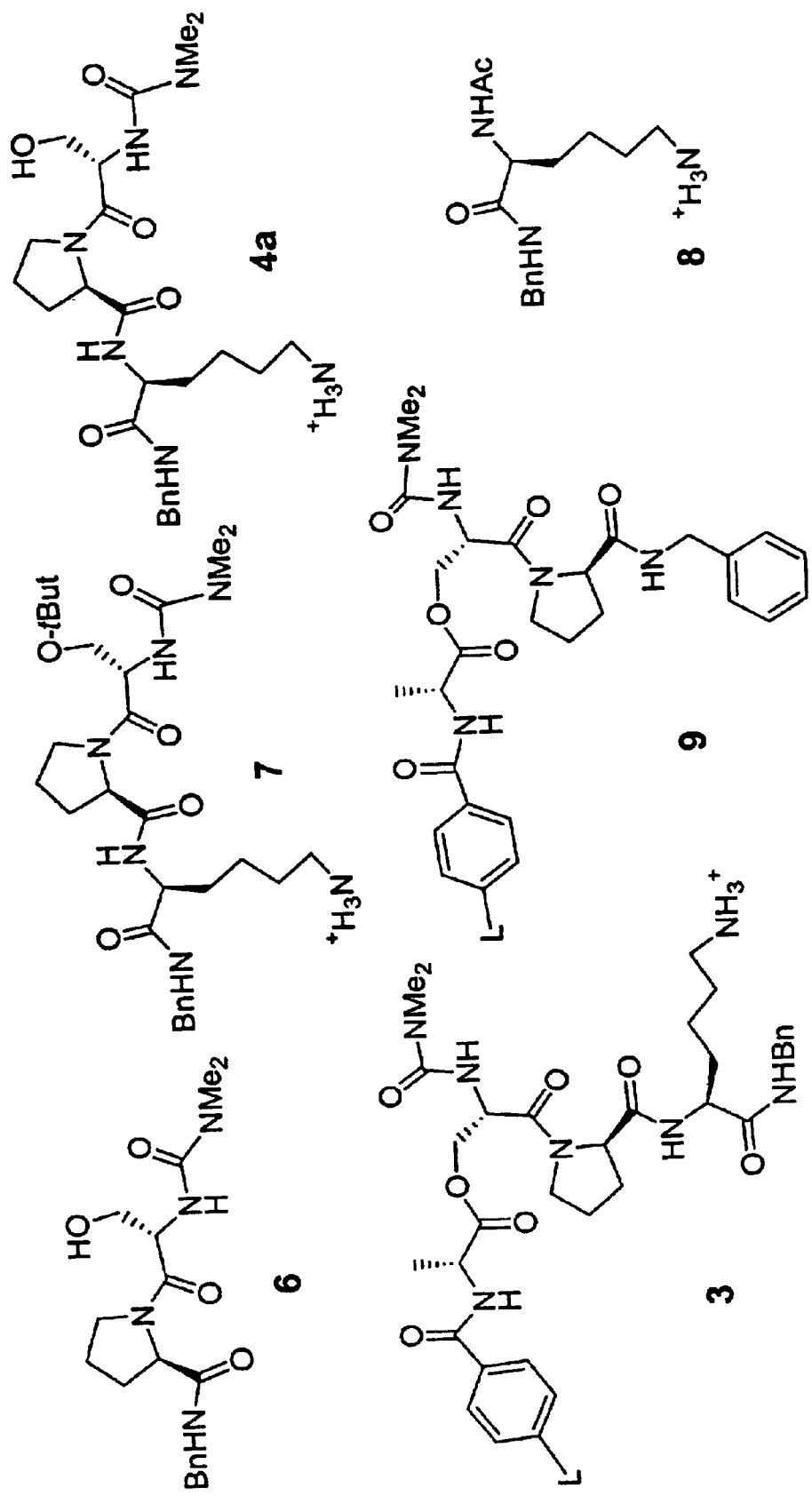
FIG. 3. Schematic representation of the small molecules assayed with the depsipeptide and the intermediate resulted by the nucleophilic attack of the serine.

The peptide 4a and the depsipeptide derivative 5 were prepared in solution (FIG. 3 and Scheme 2). The need to replace the substrate 1 with 5 emerged because of the poor solubility of 1 in water.

The ability of peptide 4a in cleaving the substrate 5 was assessed in aqueous phosphate buffer pH=7 at 37° C. Stock solutions of 16 mM of 5 and 130 mM of peptide were made in water. Phosphate buffer solution of 25 mM was made by adjusting the pH of a $K_2HPO_4$ solution to 7.0 by addition of concentrated HCl. To a 1.5 mL glass vial (Waters) were added 5 μL stock solution of 5 and 15 μL stock solution of peptide, followed by 135 μL buffer. The volume was adjusted to 160 μL by addition of water. Vials were kept in an incubator at 37° C. and 2 μL aliquots were taken every 3 h. Each aliquot was diluted with water to 5 μL and 2 μL were injected in HPLC. Separation of components was carried out on a reverse phase column C18 (Waters) using a gradient water/acetonitrile (0.1% TFA).

Figure 4:
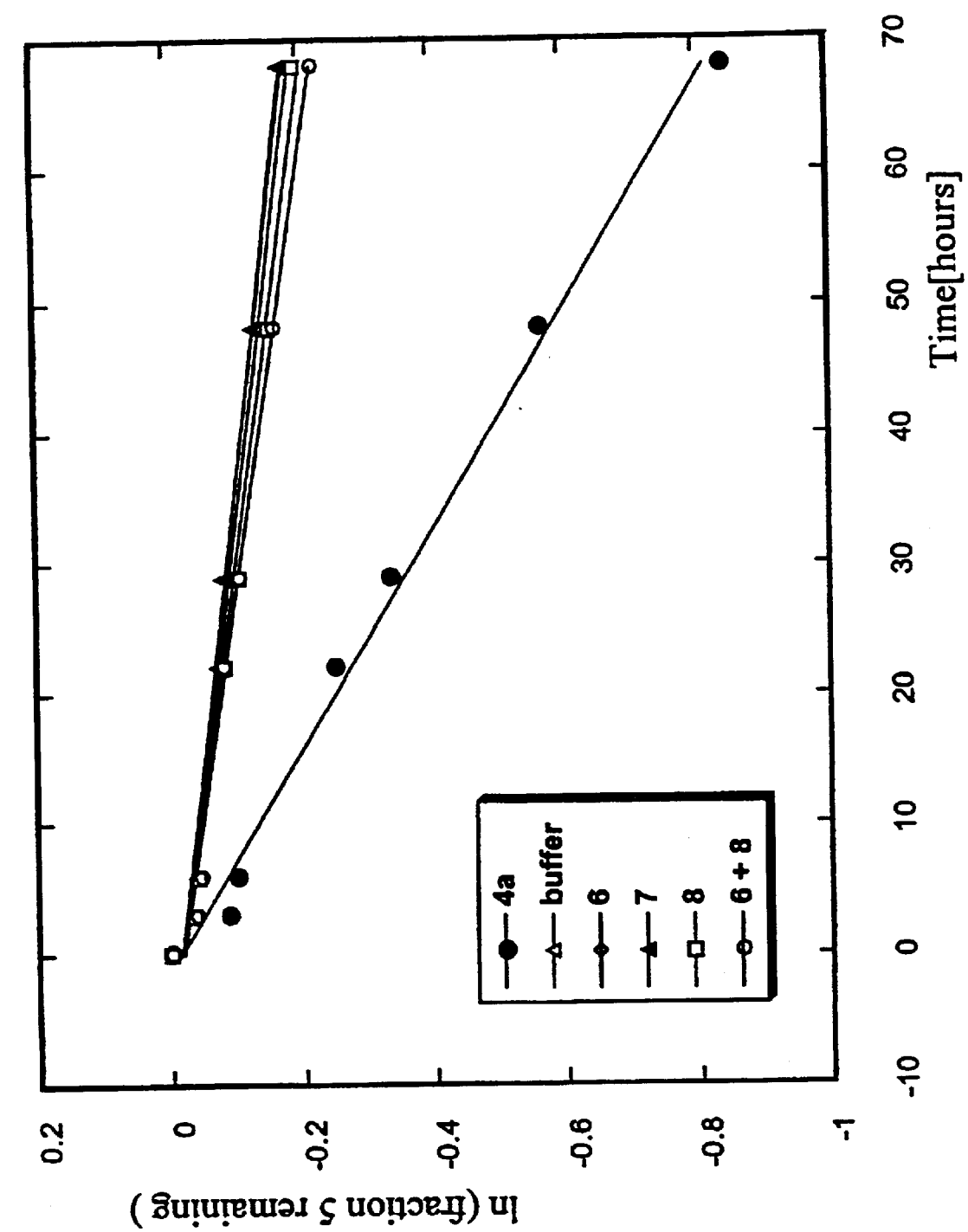
FIG. 4. Representative kinetic data for the hydrolysis of depsipeptide derivative 5 by 20 mM phosphate buffer (pH=7.0) (triangles), BnNHL-Lys-D-Pro-L-Ser dimethylurea 4a (filled circle), control sequence 6 (diamond), control sequence 7 (filled triangle), control sequence 8 (box), control sequences 6+8 (circle). Assays were performed with depsipeptide derivative 5 at 0.5 mM, while peptides were run at 12 mM. The graph is the average of five separate runs.

Using HPLC and monitoring the p-$NO_2$-phenyl derivative by UV at 275 nm, we could easily follow the disappearance of D—Ala—D—Lac derivative 5 and the formation of the hydrolyzed product 4. Under these conditions, we observed a 20% cleavage of the depsipeptide in 24 hrs. No significant effect on the rate of hydrolysis over buffer was observed using the control sequences 6, 7, 8 alone or 6 and 8 combined (FIG. 4). This proves that the whole structural assembly is necessary for the reaction to occur and that the reaction is not an artifact resulted by a change in the pH of the media due to the presence of the amine functionality.

The enantiomer of 4a was synthesized through the same procedure and its ability to cleave the depsipeptide was measured. The data obtained (not shown) suggests that the enantiomer is less than half as active as 4a. This observation explains why the enantiomeric peptide D—Lys—L—Pro—D—Ser dimethylurea was never found as an active sequence in the combinatorial library assays. The presence of a well-oriented assembly of a nucleophile and electrophile is essential but not sufficient for the reaction to occur; chiral complementary between the depsipeptide and the cleaving molecule is also required and suggests the formation of a complex between the two molecules prior to the cleavage of the ester.

Mechanistic Studies

To prove that the reaction occurs via a nucleophilic attack by serine, the cleavage of 1 by 4a was studied in THF-5% water, media in which the transesterification product 3 could be observed (Scheme 3).

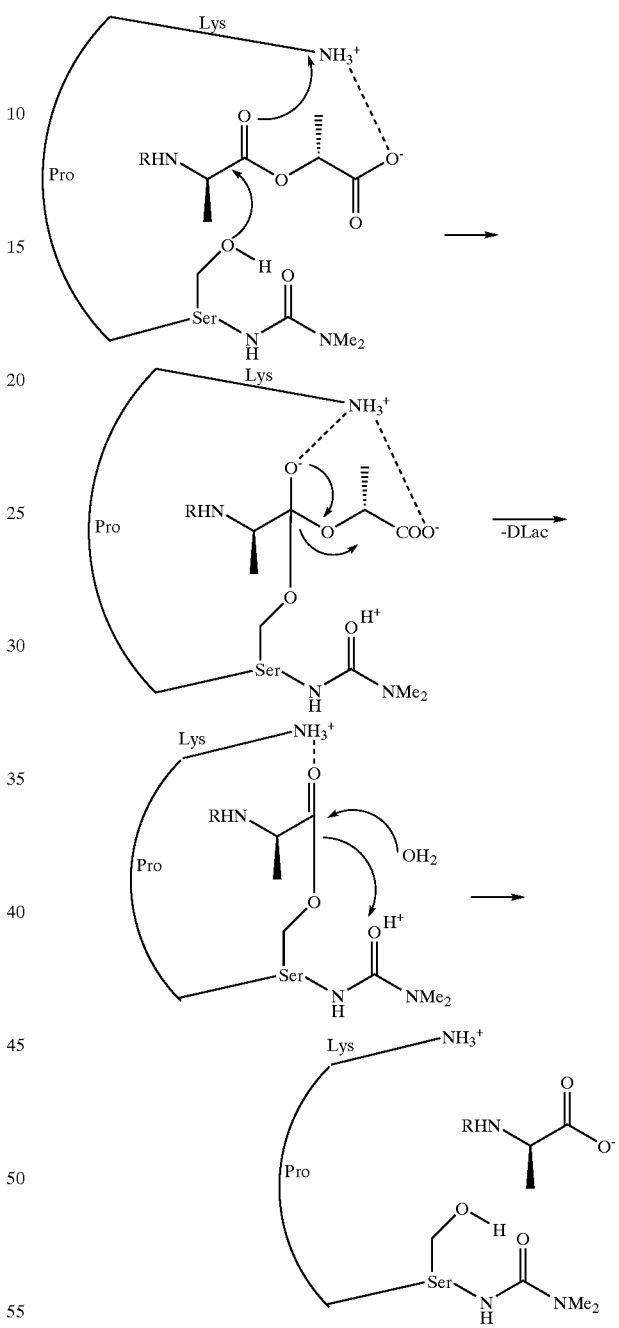

Scheme 3. Proposed mechanism for the catalytic cleavage of D—Ala—D—Lac by 4a.

Figure 15:
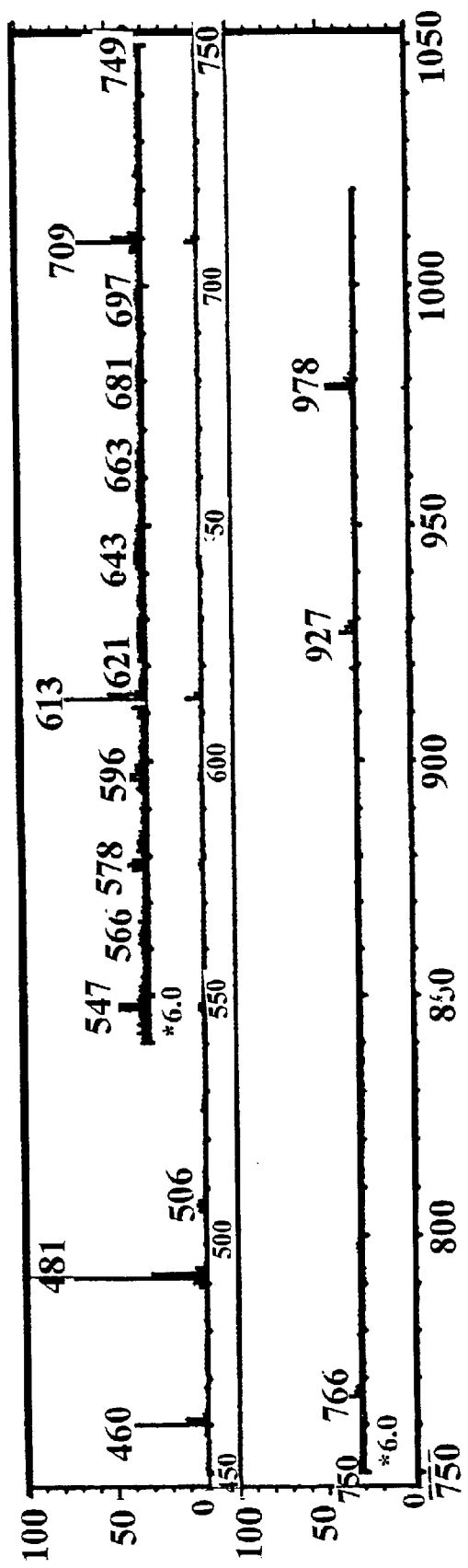
FIG. 15. MS (FAB) of the THF-water assay mixture; m/z=491 (M+1) for BnNHL—Lys—D—Pro—L—Ser dimethylurea 4a, 506 for D—Ala derivative 4, 578 for substrate 1 and 978 for transesterification product 3.
Figure 16:
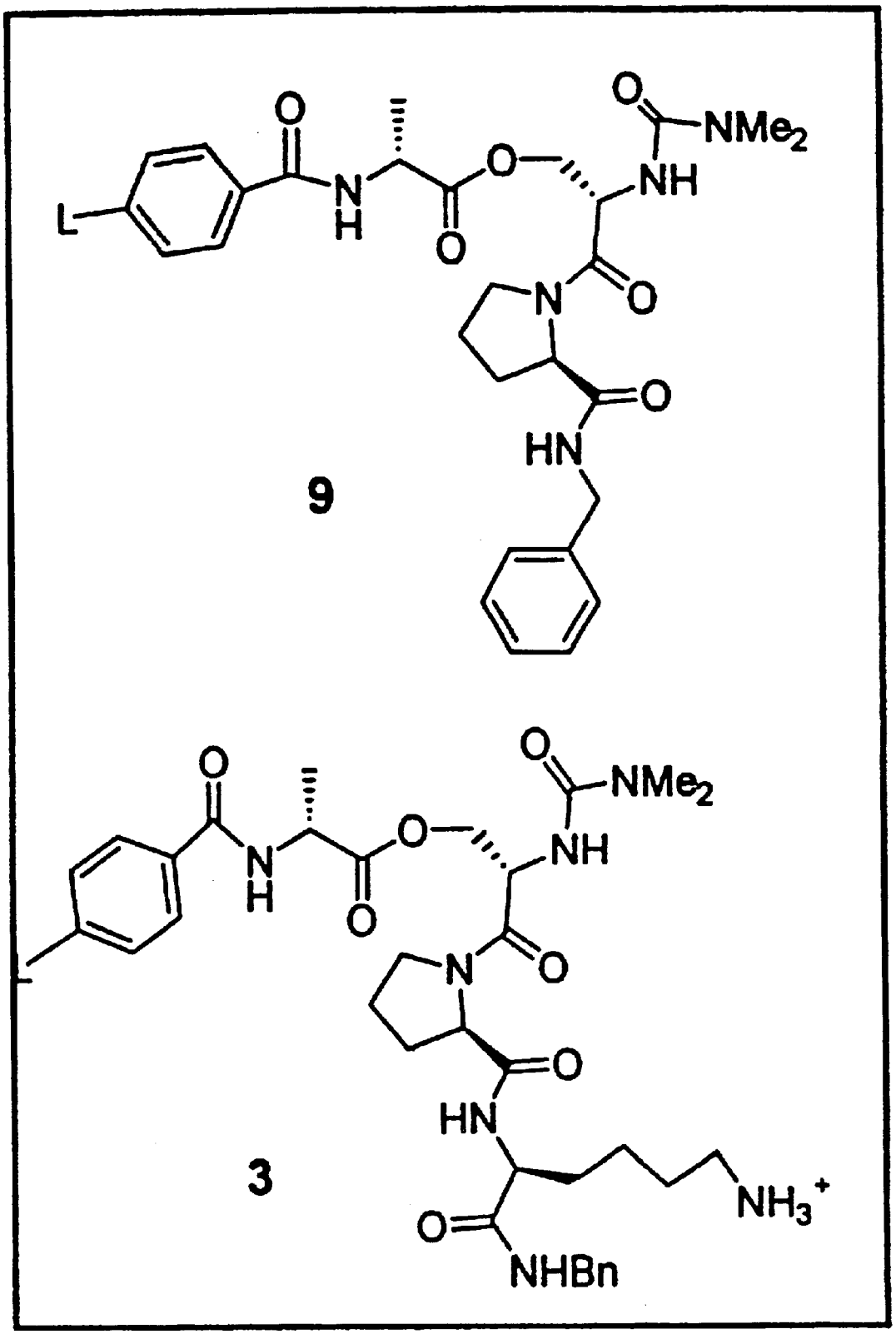
FIG. 16. Schematic representation of the intermediate resulted by the nucleophilic attack of the BnNHL—Lys—D—Pro—L—Ser dimethylurea 4a serine on analog 1 and the $^1$H NMR model compound.
Figure 17:
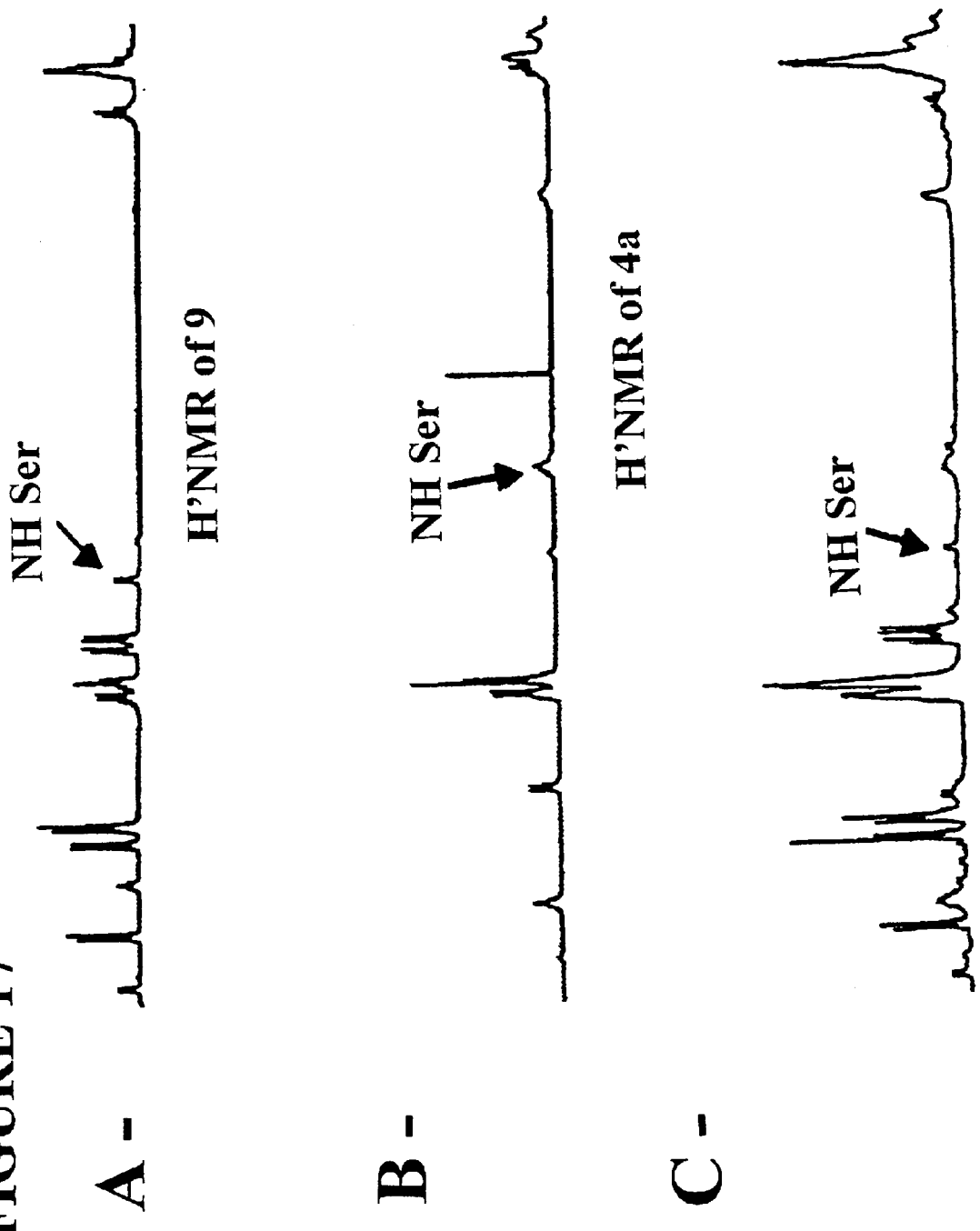
FIG. 17. Representation of the $H^1$ NMR spectra (A) of compound 9, (B) of BnNHL—Lys—D—Pro—L—Ser 4a and (C) of THF-5% water assay mixture.

The reaction could be monitored by HPLC at 485 nm, and the separation of the three components was easily performed on an analytical reverse phase column using a gradient of acetonitrile:water. Stock solutions of 2 mM concentration of 1 in THF and 49 mM of 4a (lyophilized from PIPES buffer pH=7.0) in water were prepared. In three ampoules were added 40 μL solution of 1, 7 μL of 4a and the volume was adjusted to 160 μL with THF. For background measurements, in another three ampoules 7 μL water were added instead of 4a to the solution of 1. All six ampoules were sealed under an argon stream and placed in an oil bath heated at 60° C. For each measurement one vial was opened and 5 μL were taken, diluted with 5 μL THF and 2 μL of this solution were injected in the HPLC. Isolation of the intermediate 3 proved to be however, more difficult. Application of the assay mixture to a size exclusion column (Sephadex LH-20 with DMF) gave a fraction enriched in 3, and this was used for a COSY-$^1$H NMR analysis (FIG. 16). Comparison of the NMR spectra of 4a, 3 and 9 confirmed the identity of the intermediate 3 (FIG. 17). Mass spectrum analysis (MS) was used to additionally establish the identity of the three peaks seen in the HPLC chromatogram (FIG. 15).

Small Molecule Development

The peptides resulted from the non-biased combinatorial libraries screenings are not useful as therapeutic agents due to their low catalytic activity. Additionally, they are easily destroyed by proteases. The goal of such screens was to gain an understanding of the key elements required for selective and catalytic cleavage of the altered termini and then assemble them in a simple structure.

Figure 5:
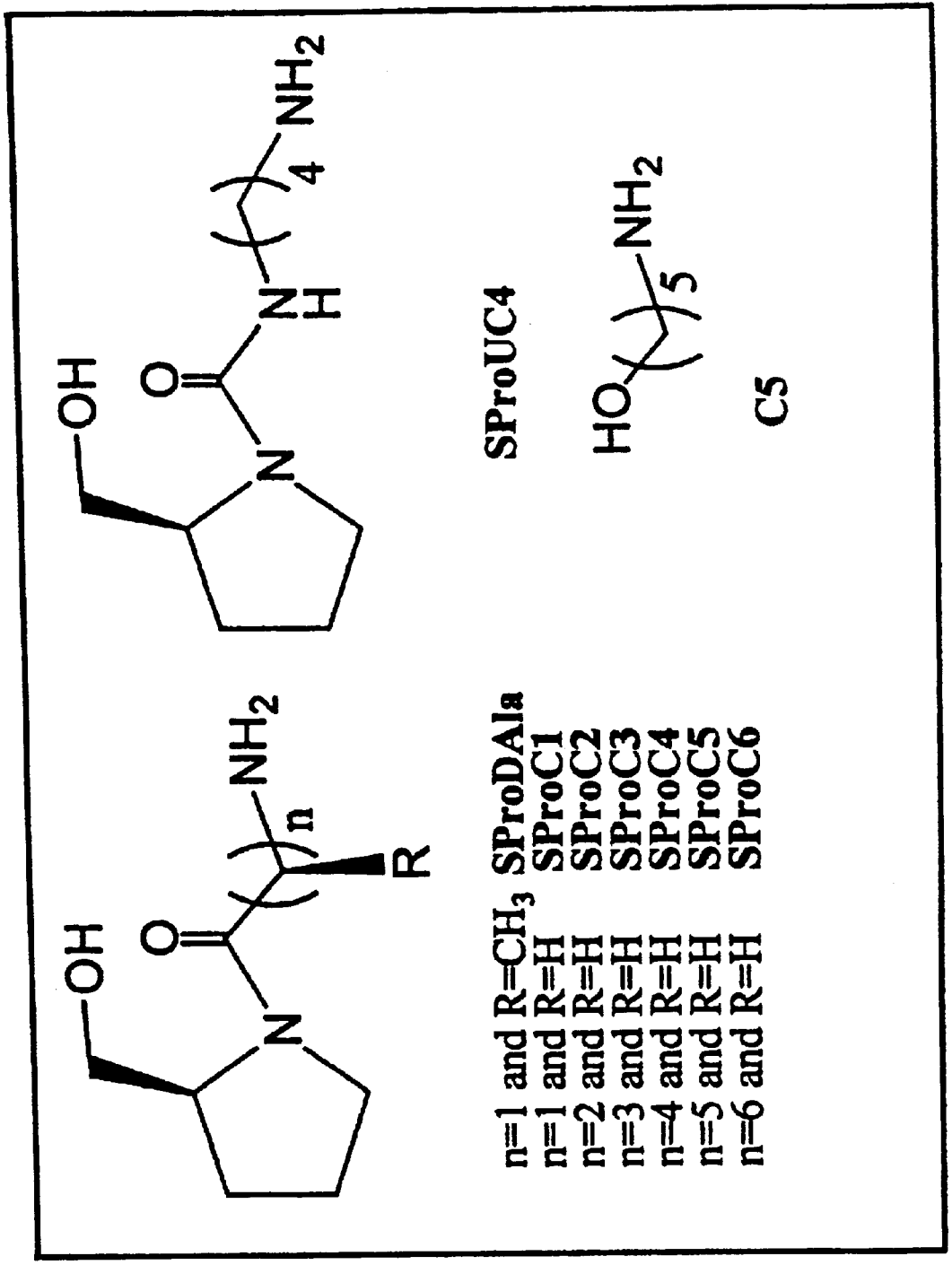
FIG. 5. Schematic representation of the S-prolinol derivatives.
Figure 6:
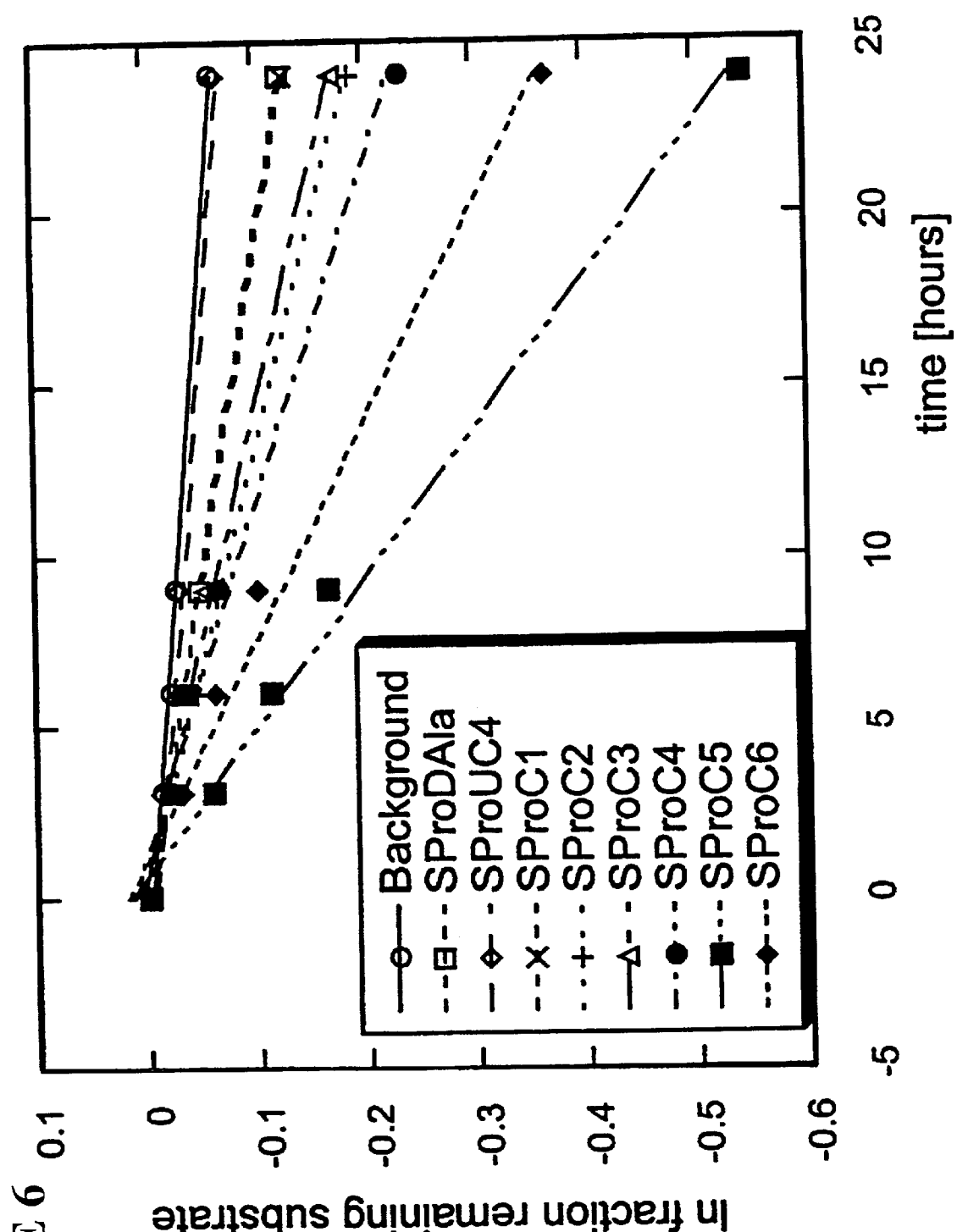
FIG. 6. Representative kinetic data for the hydrolysis of depsipeptide derivative 5 by 20 mM phosphate buffer pH=7.0 (circles), SProDAla (squares), SProUC4 (diamonds), SProC1 (asterisks), SProC2 (crosses), SProC3 (triangles), SProC4 (filled circles), SProC5 (filled squares), SProC6 (filled diamonds).

If our observations are correct, a small molecule that has a hydroxyl (serine-like functionality) of enhanced nucleophilicity, a well-oriented electrophile and a complementary chirality to the depsipeptide should catalyze the cleavage of the D—Ala—D—Lac with an efficacy comparable to the small peptide 4a. N-acylated prolinol derivatives (FIG. 5) are the simplest structures that could fulfill such requirements. Their primary alcohol functionality forms an internal H-bond with the amide, the structures allow for the addition of the electrophile ($NH_2$) through various linkers and moreover, are chiral molecules. The derivatives were tested for their ability to cleave 5 in aqueous phosphate buffer pH=7.0 at 37° C. (FIG. 6). Addition of 12 mM SProC5 induces the cleavage of 50% of depsipeptide in 24 hrs, implying that the SProC5 derivative is twice as active as the initial peptide 4a. One explanation for the higher activity of the very simple molecule SProC5 compared to 4a is the enhanced nucleophilicity of its hydroxyl (H position in $H^1$ NMR 7.59 ppm vs 6.62 ppm). Activity declines in the series with the decrease of the chain length from 5 carbons to 1 carbon. This result can be explained not only by a decrease in efficiency of the terminal amino in reaching to the carboxylate and ester of D—Ala—D—Lac with the shortening of the chain, but also by the decrease in nucleophilicity of the hydroxyl. A 6 carbon chain is also less active. The lower activity of SProC6 is probably due to the higher flexibility of the carbon chain that does not render the amino group available for the reaction. To confirm these speculations we compared the chemical shifts of the OH and NH in the $H^1$ NMR spectra of the NHBoc protected SProCn series (Table 1).

Substrate 5 was used at 0.5 mM, while prolinol derivatives were run at 12 mM. The graph is the average of three separate assays (FIG. 6).

The study shows that there is a competition between the amino group and the hydroxyl for hydrogen bonding to the amide. With the decrease of the chain length, the probability of the OH being hydrogen bonded decreases substantially, fact reflected in the chemical shifts of the OH and NH with the change in the length of the carbon chain.

TABLE 1

Shifts in the position of OH and NHBoc with the modification of the carbon chain length

| Boc-derivative | OH position (ppm) | NH position (ppm) |
|---|---|---|
| SProC1 | 4.57 | 5.48 |
| SProC2 | 4.98 | 5.28 |
| SProC3 | 4.96 | 4.75 |
| SProC4 | 5.11 | 4.65 |
| SProC5 | 5.14 | 4.54 |
| SProC6 | 5.28 | 4.52 |
| SProUC4 | 4.86 | 4.65 |

The table also explains the low activity of SProUC4, derivative in which the amide is replaced by urea. The urea is a better acceptor than the amide and should increase the reactivity of the hydroxyl. However, it is possible that structural constraints imposed by the urea play an important role and do not allow for proper orientation for H-bonding.

Figure 7:
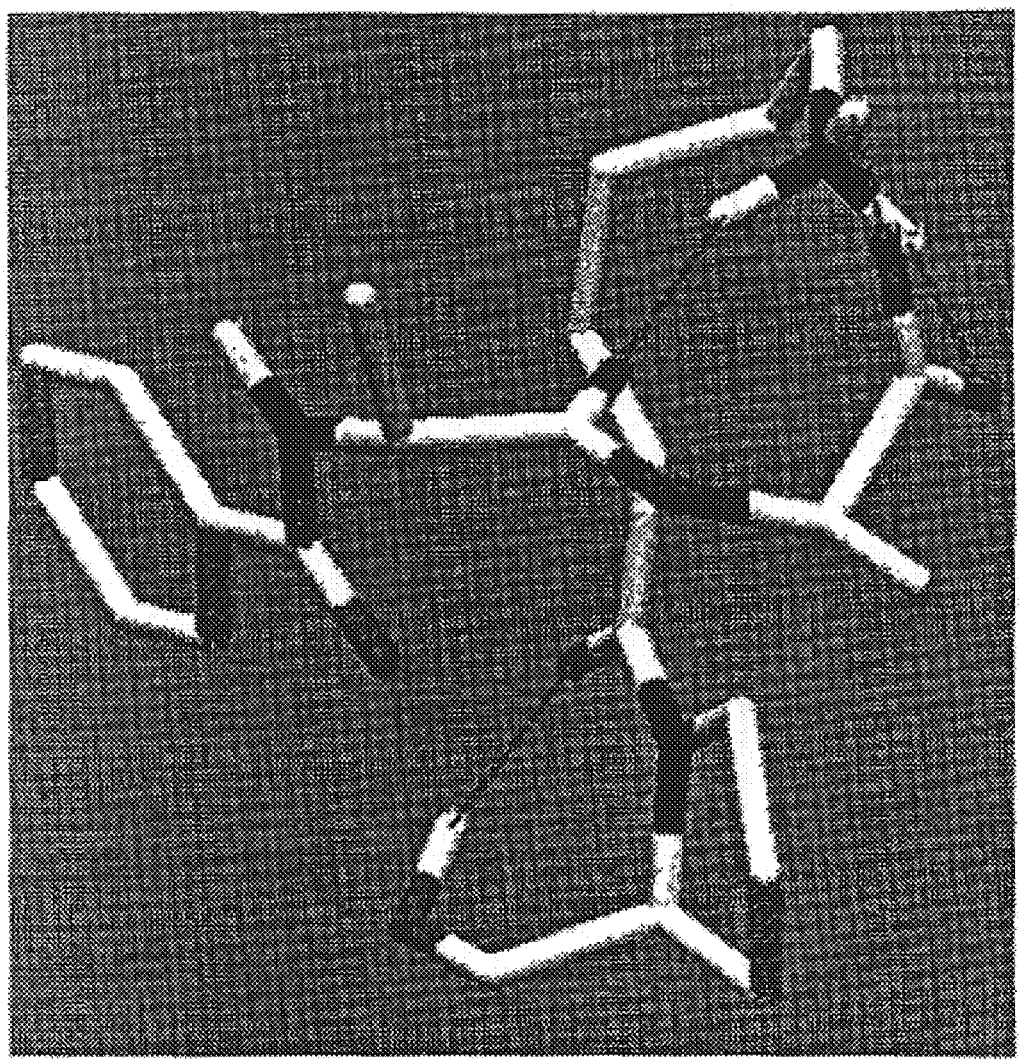
FIG. 7. Structure of the complex of PhD—Ala—D—Lac with SProC5 as calculated by molecular modeling. Hydrogen bonds are depicted by dashed lines.

Molecular modeling performed on the complex of SProC5 and PhD—Ala—D—Lac additionally confirms the structural fit of this small molecule for the cleavage of the depsipeptide (FIG. 7).

In vivo Testing of the Small Molecules against VRE

The designed small molecules should theoretically enhance the biological activity of vancomycin by reducing the pool of C-terminal altered cell wall precursors in bacteria that have intrinsic or acquired resistance to vancomycin. Therefore, to test the activity of the synthetic molecules, we used as reference organism a vanA enterococci, strain EF228 (22), and for comparison, the susceptible reference strain enterococci JH2-2 (23). SProC5, the best candidate molecule was studied in combination with vancomycin. *Enterococcus faecium* EF228 (22), a vanA strain and *Enterococcus faecalis* strains JH2-2 (23) were grown on BHI (Difco or Oxoid) agar or broth at 37° C. Biological assays were performed in 96-well tissue culture plates (MICROTEST U-bottom, Falcon, Becton Dickinson). A range of vancomycin (Sigma) concentrations (100 μl per well) was used based on sequential two-fold dilution starting from 100 and 2000 μg/ml to 0.1 and 1.96 μg/ml for strains JH2-2 and EF228, respectively. The different molecules were added (100 μl per well) at fixed concentrations (0, 5, 10, 50 and 100 mM) containing an inoculum of either strain at a final dilution of $10^{-2}$ obtained from an overnight culture. The range of effective vancomycin concentrations started at 50 and 1000 μg/ml for JH2-2 and EF228, respectively. Microtiter plates were incubated at 37° C. without agitation for 18 hours. Cell sediments were resuspended by shaking and optical density at 600 nm was measured with an ELISA Multiskan RC plate reader (Labsystems, Helsinki, Finland). Bactericidal activity was determined by serially diluting ($10^{-2}$, $10^{-4}$ and $10^{-5}$) each well in BHI broth and plating 10 μl of each dilution on BHI agar plates. Plates were incubated 24 hours and the number of colony forming units per ml was determined.

A reduction of 10% in the load of altered termini should theoretically decrease the MIC of vancomycin by 10-fold.

FIG. 8 illustrates the specific synergistic effect of SProC5 against the vanA strain EF228. Panel A shows that vancomycin alone inhibited growth at 500 μg/ml while SProC5 (50 mM) combined with vancomycin reduced the minimum inhibitory concentration to 62.5 μg/ml, i.e. a 8–16 folds decrease in the MIC. Bactericidal activity was confirmed by determining the number of cells that survived the combined treatment of vancomycin and SProC5 (FIG. 8A, black bars).

Figure 8A:
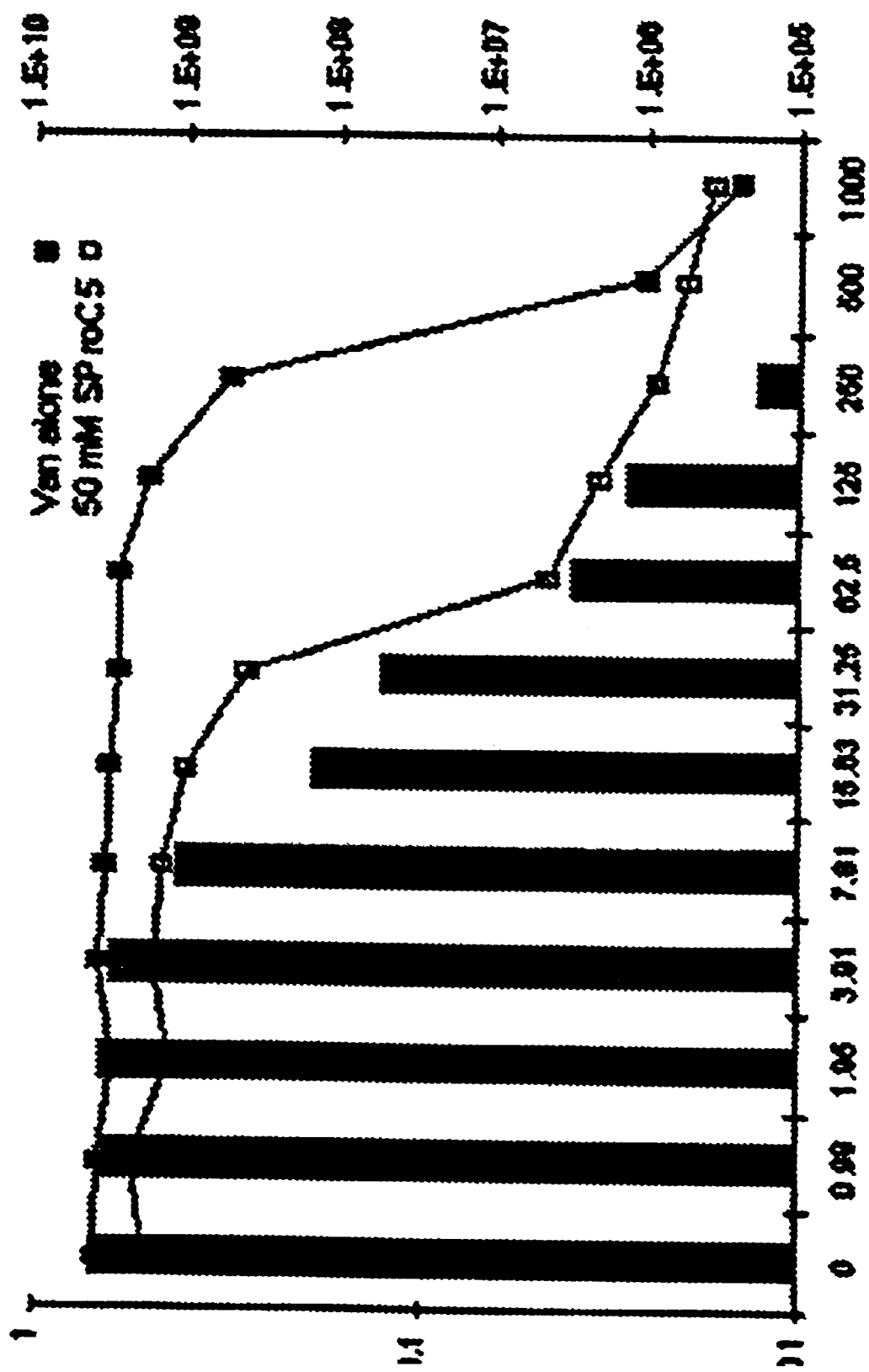
FIGS. 8A–8D. Illustration of the specific synergistic effect of SProC5 against the vanA strain EF228. A) Strain EF228 was grown in the presence of increasing concentration of vancomycin with (open squares) or without (solid squares) the small molecule SProC5 (50 mM). Bactericidal activity was estimated by determining the number of colony forming units per ml (CFU/ml) that survived the combined treatment of vancomycin and SProC5 (solid bars). B) Two structurally related molecules SProC2 (solid symbols) and SProC5 (open symbols) were compared for their relative synergy with vancomycin. Their activities were concentration dependent (0, 5 10 and 50 mM, represented by square) with SProC5 being the most efficient molecule mirroring the kinetic assays (see FIG. 6). C) SProC5 specificity together with vancomycin against strain EF228 was tested by comparing to its enantiomer RProC5 or its 5 carbon unit C5. Results represent the average of four independent experiments at the fixed concentration of 100 mM. D) Strain JH2-2 was used as a representative of vancomycin susceptible strains that do not synthesize altered D—Ala—D—Lac terminating cell wall precursors.
Figure 8B:
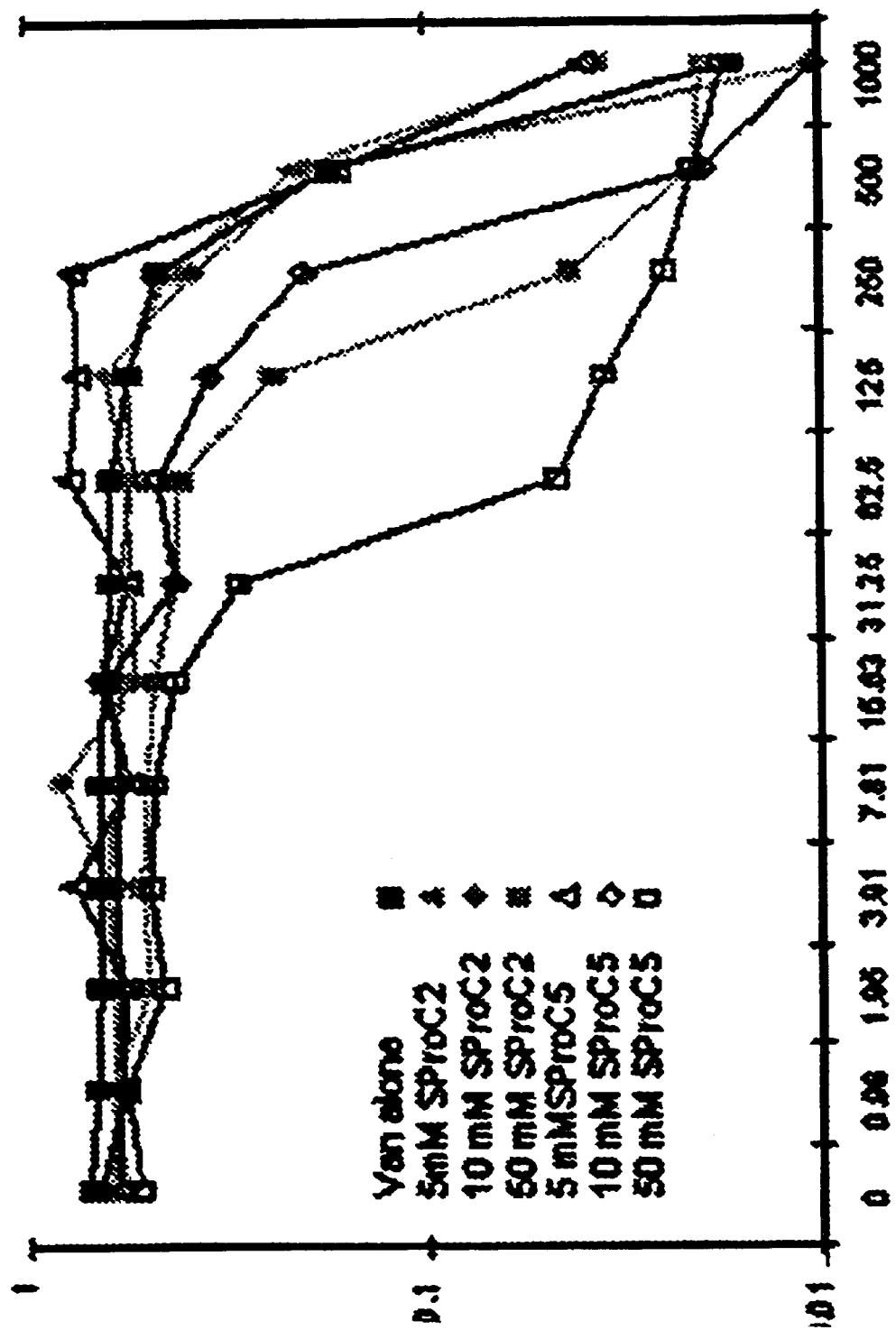
Figure 8C:
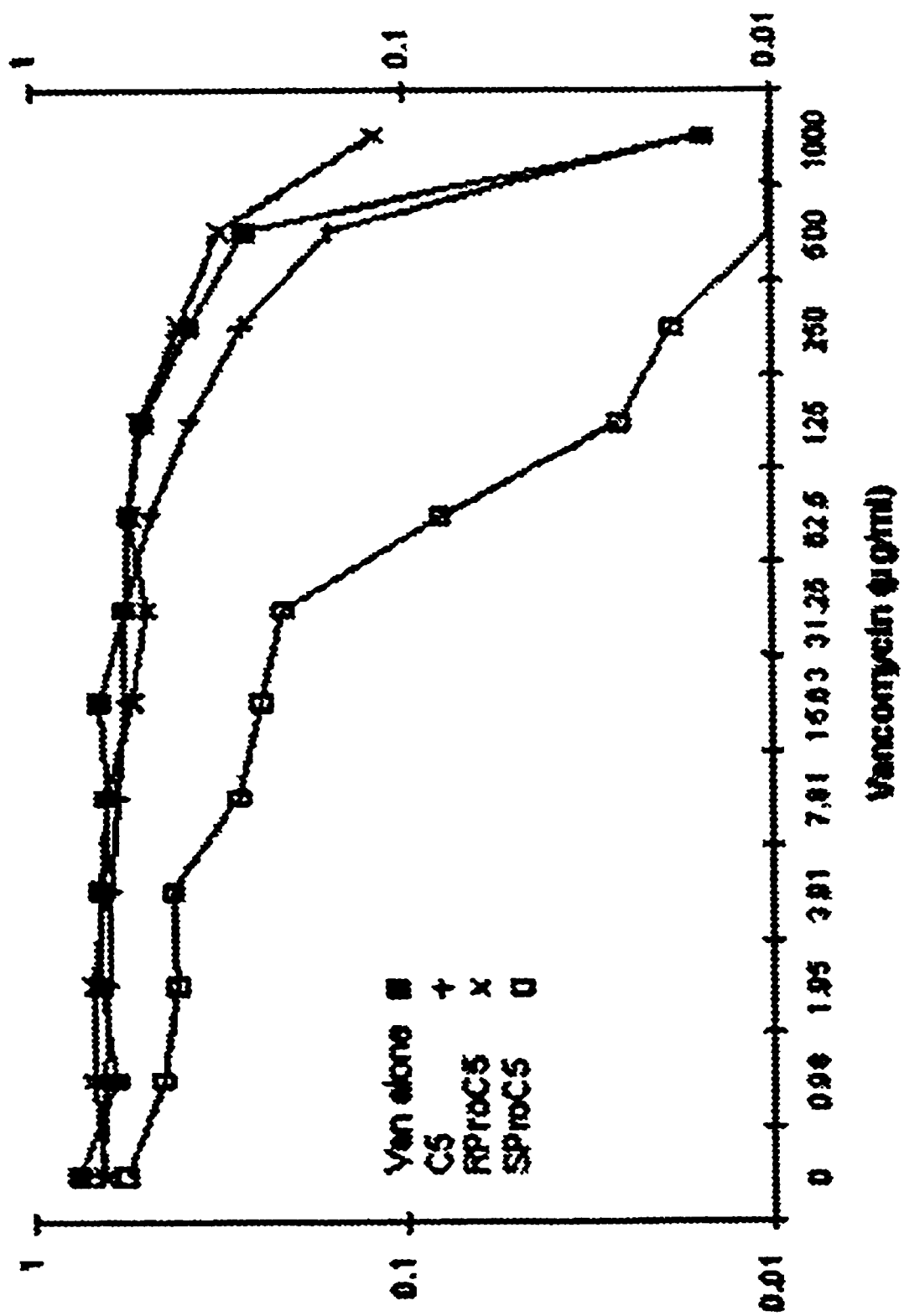

Indeed, the combination of 62.5 µg/ml of vancomycin with 50 mM of SProC5 resulted in a three log decrease in bacterial load compared to vancomycin or SProC5 alone. This value was increase to four log when 250 µg/ml of vancomycin was used with 50 mM SProC5. The synergistic effect of SProC5 was dose dependent as shown in FIG. 8B (5 mM of SProC5 was ineffective while 10 mM had an intermediate activity).

Specificity of SProC5 mode of action against D—Ala—D—Lac termini is reinforced by the complete absence of increased sensibility of JH2-2 to vancomycin by SProC5, SProC2 or any of the control molecules, even at 100 mM. Results represent the average of two independent experiments (FIG. 8)

SProC5 alone had no inhibitory or bactericidal activity against enterococci (see FIG. 8). Its synergistic effect with vancomycin could be related to a distinct mechanism than the one predicted based on the specific hydrolytic activity of SProC5. To validate the mechanism, we compared SProC5 activity to a related molecule SProC2 characterized by a lower D—Ala—D—Lac hydrolytic activity in our kinetic assays (see FIG. 6). Indeed, as predicted from the hydrolytic activity, SProC2 had a much lower synergistic effect with vancomycin although not negligible (at 50 mM, MIC to vancomycin decreased to 250 µg/ml). SProC2 was able to decrease the MIC to vancomycin only by 2 to 4 folds in the conditions tested (see FIG. 8B).

Further evidence correlates the hydrolytic activity of SProC5 with its synergy with vancomycin. SProC5 activity was compared to that of its enantiomer molecule RProC5 and to its corresponding 5 carbon unit (C5). None of the control molecules had a synergistic effect with vancomycin even at 100 mM (see FIG. 8C) strongly suggesting that the basis for the biological activity of SProC5 was derived from its enhanced and specific D—Ala—D—Lac hydrolytic activity.

Figure 8D:
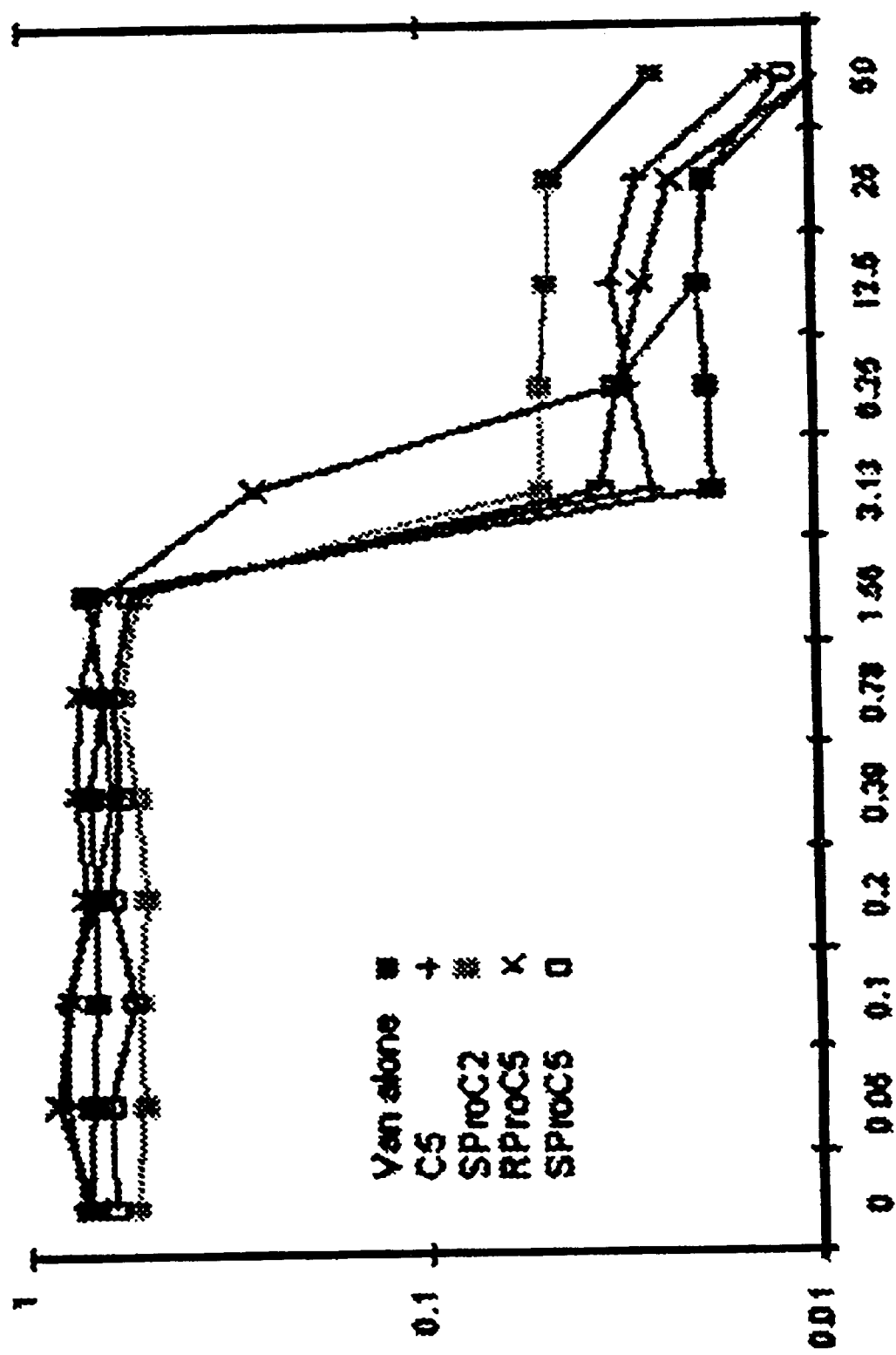

Finally, strain JH2-2 which is susceptible to vancomycin and does not synthesize altered cell wall precursors, was used as a control. The sensitivity of JH2-2 to vancomycin was unaffected by the presence of any of the synthetic molecules (SProC2, C5, RProC5 and SProC5) even at 100 mM (FIG. 8D). MIC of vancomycin was unchanged in any of the tested conditions (MIC between 1.58 and 3.13 µg/ml).

Through screening of combinatorial libraries and the study of the active sequences and patterns, an understanding of the essential key elements for catalytic and selective cleavage of D—Ala—D—Lac is achieved. Assimilation of these features resulted into the design of a simple small molecule that is more effective in cleaving the depsipeptide than its paternal small peptide 4a. This molecule, SProC5, increases the sensitivity of vanA resistant bacterial strain to vancomycin. Our in vivo results suggest that SProC5 enhances vancomycin's activity because of its D—Ala—D—Lac's hydrolytic activity. The synergistic effect of SProC5 mirrors its ability to hydrolyze the depsipeptide bond. Several observations support this hypothesis. First, a related compound SProC2, which has a lower hydrolytic activity, is less efficient in enhancing vancomycin's inhibitory activity as predicted from the kinetic studies. Furthermore, the enantiomer of SProC5—RProC5—lacks any synergy with vancomycin. Finally, the enterococcal strain JH2-2 which is unable to synthesize altered cell wall precursors was completely insensitive to the activity of the synthetic molecules. Taken together, these data suggest that the mechanism of synergy in vivo is based on the hydrolytic capability of the synthetic compound SProC5.

SProC5 can reverse resistance in several ways. It could similarly as VanX to reduce the cytoplasmic pool of D—Ala—D—Lac at every step of the biosynthetic pathway, therefore favoring the synthesis of normal cell wall precursors terminating in D—Ala—D—Ala.

Alternatively, SProC5 could remain extracellular and actively hydrolyze cell wall lipid-intermediates. Lipid intermediates would be truncated as disaccharide-tetrapeptides, an accumulation which would result progressively in a hypocrosslinked peptidoglycan. E.coli mutants that are unable to properly recycle tetrapeptide turnover products, accumulate tetrapeptide derivatives resulting in lysis and death in stationary phase (24).

A third mechanism can be envisioned. The resistance phenotype in vanA strains is inducible and dependent on a two-component regulatory system. VanS and VanR function as a sensor and a response regulator, respectively. The suggested signal sensed by VanS appears be the accumulation of lipid II (undecaprenyl-disaccharide-pentatpeptide) (25–27). The accumulation of tetrapeptide derivatives of lipid II due to SProC5 hydrolytic activity might compete for the binding site of VanS interfering with the signaling cascade and the induction of vanHAXYZ transcription.

The three hypotheses for the mode of action of SProC5 are not exclusive and could occur at the same time. A combination of muropeptide, cell wall precursor composition analysis and transcription analysis of the vanA cluster would be needed to distinguish between the different mechanisms.

Molecules that catalytically and selectively cleave the altered termini of the bacteria cell wall can disable the antibiotic-resistance mechanism in these pathogens. The molecules act by re-sensitizing bacteria to the drug and could be used in concert with vancomycin in the treatment of VRE. Additionally, this work shows that bits of information obtained from the screening of non-biased random libraries and from molecular modeling can be assimilated in the design of structurally different molecules that act by the same mechanism. One can envision that a more potent candidate for the cleavage of the D—Ala—D—Lac could result from screening biased libraries that assemble the structural characteristics described in this work. We believe the approach for identifying novel molecules able to enhance the activity of vancomycin has long term potential for the management of infectious diseases.

Combinatorial Library Assay Development

The libraries used in screening for D—Ala—D—Lac cleavers are presented in FIG. 1 and were randomly selected from the Still group archive to achieve higher structural diversity. All libraries posses amino acid building blocks, however, the variance rises from the scaffold that undoubtedly allows a structurally different organization of these building blocks. Library GLPro (28) uses 12-deoxycholic acid scaffold that allows differential derivatization of the two arms due to the distinct reactivity of the C3 and C7 hydroxyls, while library Yuan Chen (29) employs, in addition to the cholic acid core, derivatized hydroxyprolines to which the amino acids are linked. The cyclen core scaffold used for libraries MB3 and MB4 (30) contains three NH's as starting points for growing the identical three or four amino acid peptide chains, respectively. Libraries SSY (31), HW (32) and JW (33) are acylated tripeptide libraries linked to the solid support through a caproic acid unit. However, library SSY contains 15 different acylating groups, while all the members of libraries HW and JW are acetylated. All peptides were side chain deprotected and washed with dichloromethane (DCM)/triethylamine (TEA) after trifluoroacetic acid (TFA) deprotection to ensure that all possible nucleophiles were in the unprotonated state.

Figure 9A:
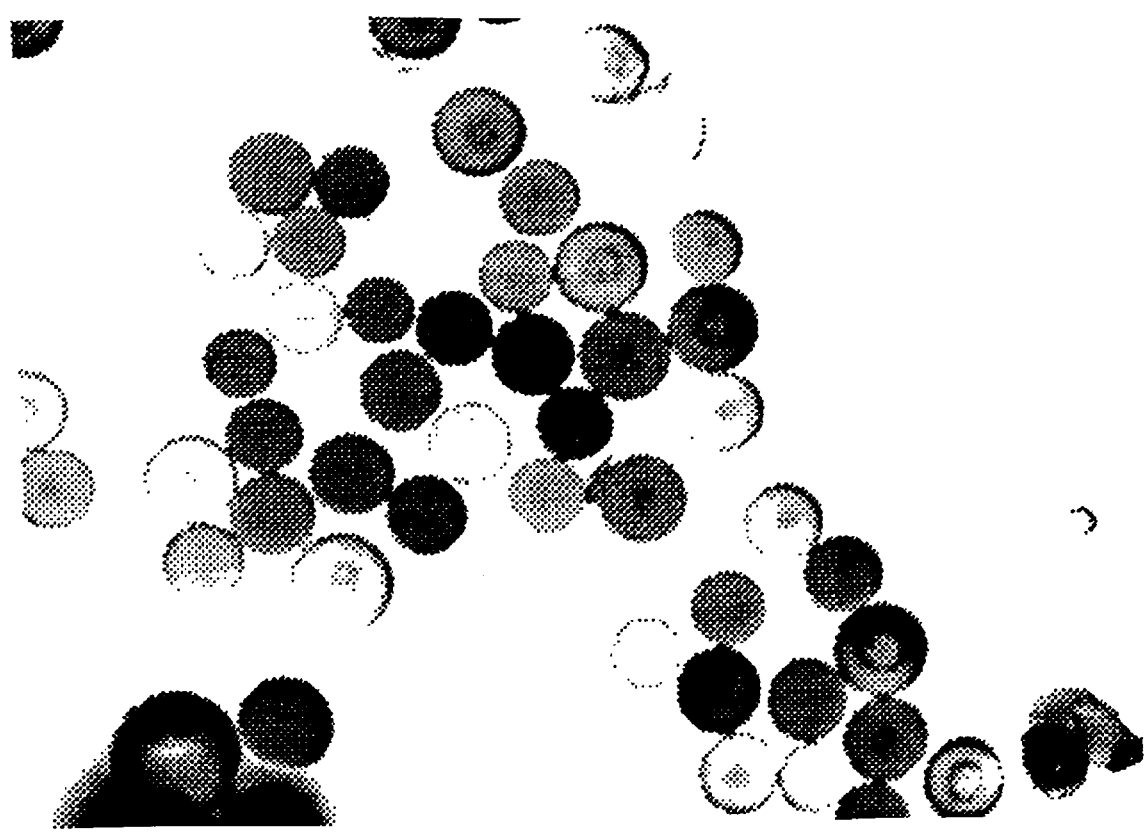
FIGS. 9A–9B. (A) Picture of a combinatorial library after screening against substrate 1 and removal of the solution (B) Picture of the same library after several DMF washes.
Figure 9B:
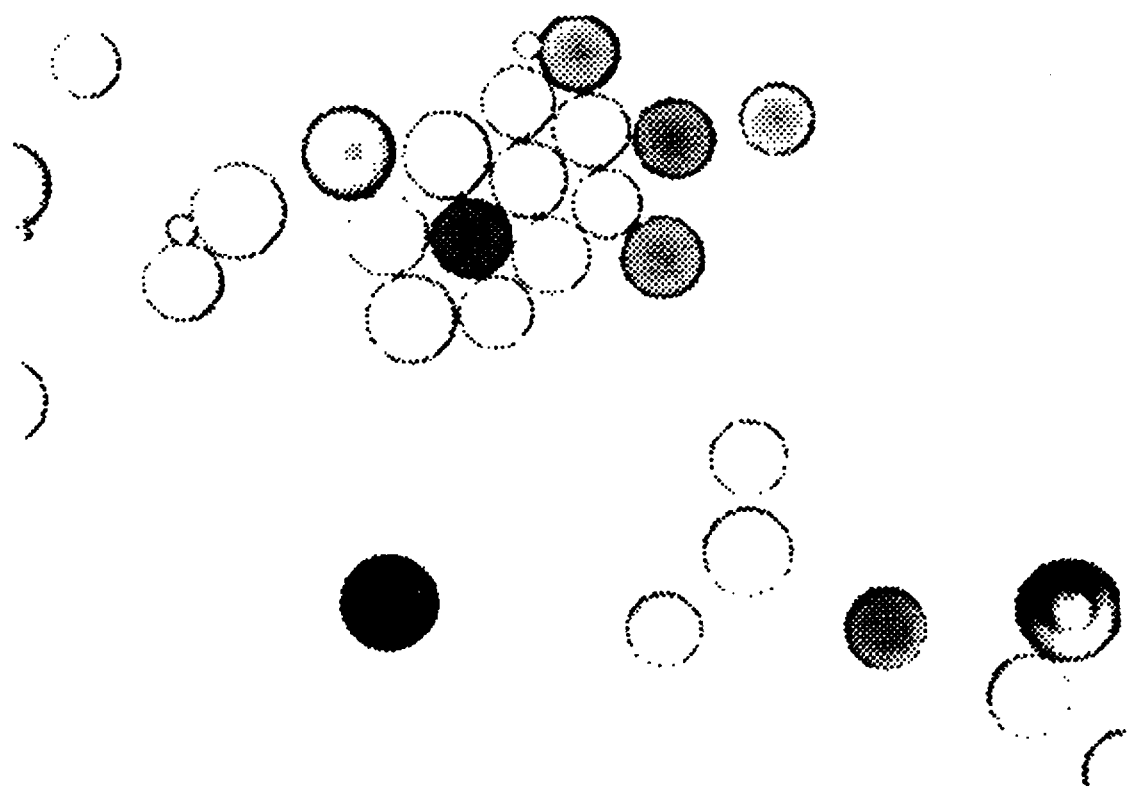
Figure 10:
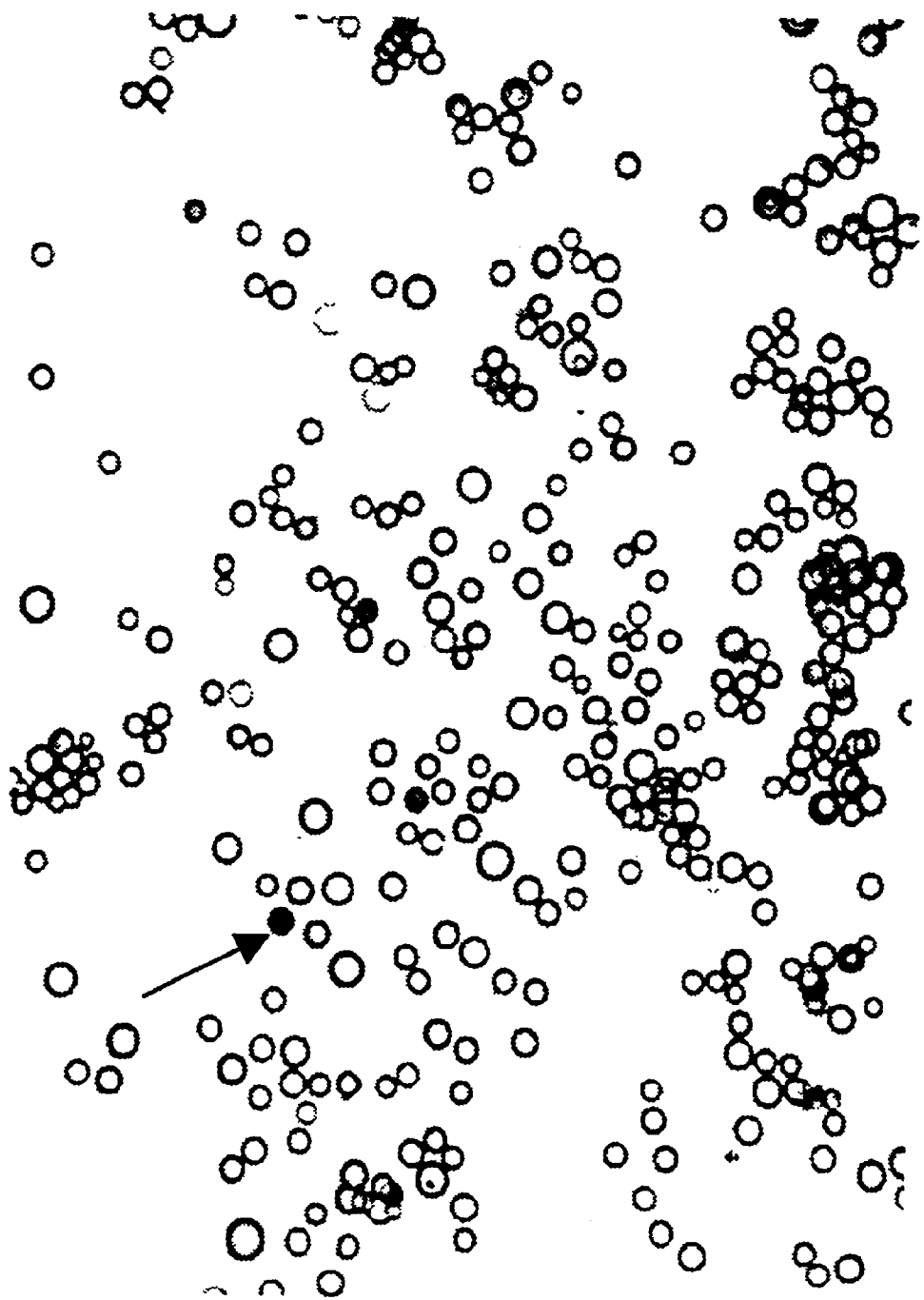
FIG. 10. Photograph of library SSY before picking the red-label carrying active beads. Assay carried out at 0.85 mM (1) in DMF. One red bead selected for analysis is pointed out in the upper-left corner of the image.

The assay for screening these libraries against 1 involved shaking a desired amount of library beads with the solution of labeled substrate for a period of time. After the reaction occured, the label-carrying beads were selected and analyzed. The initial assays were performed in 1,2-dichloroethane (12DCE) at a concentration of 2.3 mM in substrate 1. After 3 days of shaking, the beads were extensively washed with dimethylformamide (DMF) and once with a diluted solution of benzylamine in DMF to remove any physically bound substrate (FIGS. 9A and 9B).

Figure 11:
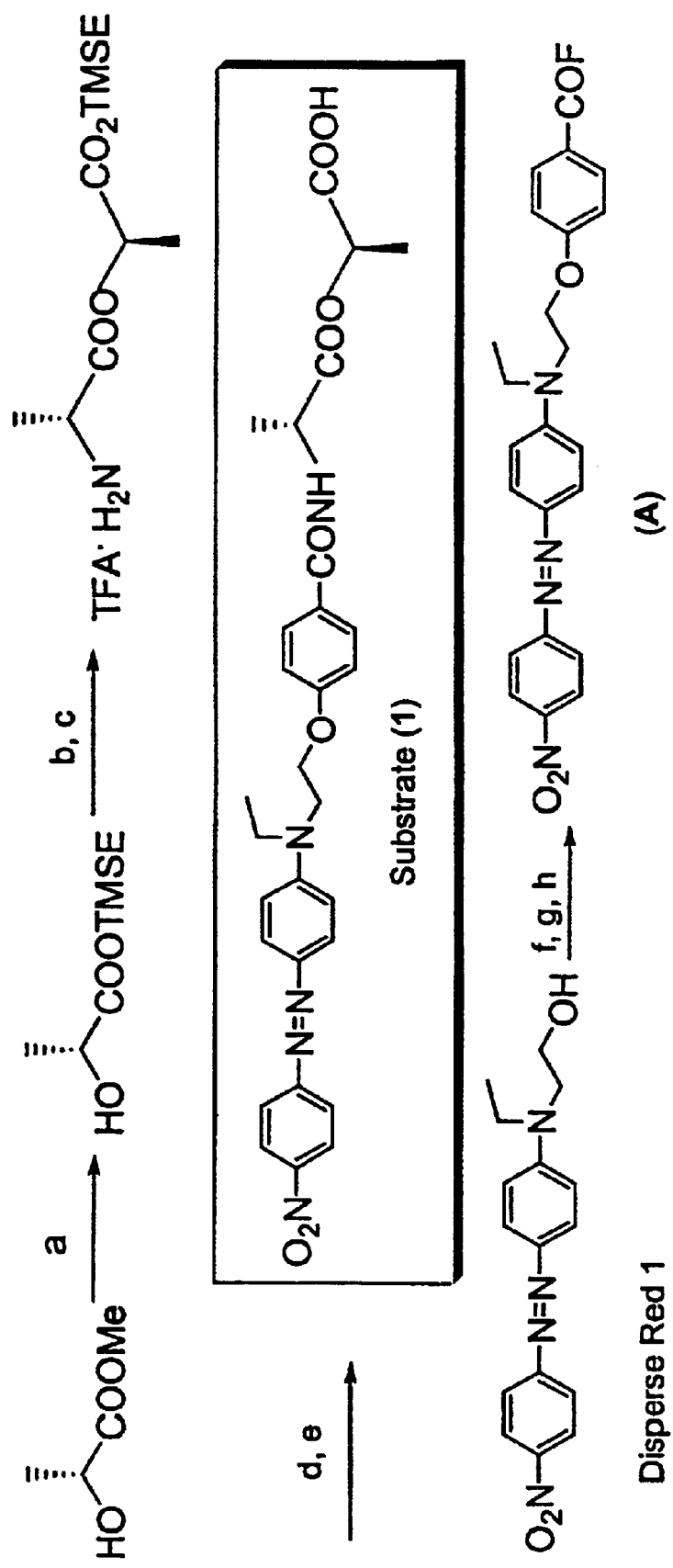
FIG. 11. Methodology utilized for the synthesis of dye-labeled depsipeptide (1)(a). 2-(Trimethylsilyl)ethanol, Ti(i-PrO)$_4$, THF; (b). BocD—AlaCOF, DIEA, DMAP, DCM; (c). TFA:DCM=4:1; (d). A, DIEA, DMAP, DCM; (e). TBAF; (f). Methyl 4-hydroxybenzoate, DEAD, PPh$_3$, toluene:DCM=5:1; (g). LiOH; (h). Cyanuric fluoride, pyridine, DCM.

To improve selectivity in the case of library SSY, assays were performed in different solvents and lower concentrations. From a choice of DCE, DCM, tetrahydrofuran (THF) and DMF, best results were obtained in DMF where selectivity and intensity of the beads were enhanced (FIG. 11). A decrease in concentration of the substrate to 0.85 mM also improved selectivity. This concentration proved to be the lower threshold for eye detection of red beads.

Results revealed that in every library the active sequences carried serine at the amino-terminal position. This finding is remarkable considering that other nucleophiles such as Thr, Lys and terminal amino functionality, present in the screened libraries, did not appear at that position in the red beads.

Additionally:

- for library GLPro, 80% of the active beads carried the sequence D-Pro—L—Pro—L—Ser on the first arm (C3), while the other 20% Gly—L—Pro—L—Ser on the second arm (C7)
- library MB3 showed activity only after previous equilibration with $Cu(OAc)_2$. Position $A_2A_3$ was always occupied by the sequence Pro—Ser, while $A_1$ was somehow variable
- library MB4 revealed only one active sequence: D—Asn—L—Lys—L—Pro—L—$SerNH_2$
- library SSY carried exclusively the dimethylurea capping group from a choice of 14 others, and the most colored beads had frequently Pro and Lys in a neighboring position to the terminal Ser
- library Yuan Cheng exhibited activity only if initially equilibrated with $Cu(OAc)_2$. Under those conditions, 85% of the active beads had the calibration mark: trans L-hydroxyPro1$A_1$–$A_2$ cis,trans-L-hydroxyPro2-D—Ser—$A_4$
- libraries HW and JW, acetylated tripeptide libraries, although carrying a larger selection of amino acids than SSY, showed no activity under the assay conditions Control assays were performed with side chain protected libraries, and additionally, with the trimethylsilyl ethyl ester (TMSE) of the substrate 1. Neither assay resulted in active sequences.

Combinatorial Assay Sequence Data

TABLE 2

Library GLPro. 0.5 copies were used (about 10,000 beads) for a 3 days assay in 12DCE with substrate 1. 15 red beads found.

| L, DPro | $A_1$ | $A_2$ | $A_3$ | $A_4$ |
|---|---|---|---|---|
| DPro | Pro | Ser | Thr | Lys |
| DPro | Pro | Ser | Lys | Ala |
| DPro | Pro | Ser | Thr | Pro |
| DPro | Pro | Ser | Thr | Ser |
| DPro | Pro | Ser | Lys | Val |
| DPro | Pro | Ser | Pro | Val |
| DPro | Pro | Ser | Val | Ser |

TABLE 2-continued

Library GLPro. 0.5 copies were used (about 10,000 beads) for a 3 days assay in 12DCE with substrate 1. 15 red beads found.

| L, DPro | $A_1$ | $A_2$ | $A_3$ | $A_4$ |
|---|---|---|---|---|
| DPro | Pro | Ser | Thr | Pro |
| DPro | Pro | Ser | Phe | Ser |
| DPro | Pro | Ser | Lys | Ala |
| DPro | Pro | Ser | Pro | Ser |
| DPro | Pro | Ser | Pro | Ser |
| DPro | Thr | Pro | Pro | Ser |
| DPro | Phe | Ser | Pro | Ser |
| LPro | Leu | Ala | Pro | Ser |

TABLE 3

Library MB3. 0.1 copies were used, about 900 beads pre-equilibrated with $Cu(OAc)_2$, in an assay performed in 12DCE with substrate 1. 7 red beads found.

| $A_1$ | $A_2$ | $A_3$ |
|---|---|---|
| LAla | DPro | DSer |
| LVal | DPro | DSer |
| LPro | LPro | LSer |
| DAsn | DPro | LSer |
| LVal | DPro | LSer |
| LAla | LPro | LSer |
| LGln | DPro | DSer |

TABLE 4

Library MB4. 0.07 copies were used (about 9,000 beads) used for an assay performed in DMF with substrate 1. 1 red bead found.

| $A_1$ | $A_2$ | $A_3$ | $A_4$ |
|---|---|---|---|
| DAsn | LLys | LPro | LSer |

Tables 5A–5C. Library SSY. (A) 0.2 copies used, about 10,000 beads, for an assay in 12DCE with substrate 1. (B) 0.2 copies used, about 10,000 beads, for an assay in DMF with substrate 1. (C) 1.5 copies used, about 80,000 beads, for an assay in DMF with 0.85 mM substrate 1. Only the very strongly red beads picked.

TABLE 5A

| $A_1$ | $A_2$ | $A_3$ | CAP |
|---|---|---|---|
| LLys | DPro | LSer | $NMe_2$ |
| LSer | LLys | LSer | $NMe_2$ |
| DPro | LLys | LSer | $NMe_2$ |
| DSer | LLys | LSer | $NMe_2$ |
| LPro | LLys | LSer | $NMe_2$ |
| LAla | DLys | DSer | $NMe_2$ |
| DPro | LPro | DSer | $NMe_2$ |
| LLys | LAla | LSer | $NMe_2$ |
| DLys | LVal | DSer | $NMe_2$ |
| LLys | DAla | LSer | $NMe_2$ |
| DLys | LAla | LSer | $NMe_2$ |

TABLE 5B

| A₁ | A₂ | A₃ | CAP |
|---|---|---|---|
| LLys | DPro | LSer | NMe₂ |
| LAsn | DPro | LSer | NMe₂ |
| LLys | LPro | DSer | NMe₂ |
| LPro | LLys | LSer | NMe₂ |
| DGln | LLys | LSer | NMe₂ |
| LSer | LLys | LSer | NMe₂ |
| LLys | DLys | DSer | NMe₂ |
| LAla | DLys | Dser | NMe₂ |

TABLE 5C

| A₁ | A₂ | A₃ | CAP | Nr. of times found |
|---|---|---|---|---|
| LLys | DPro | LSer | NMe₂ | 2 |
| DAsn | LLys | LSer | NMe₂ | 3 |
| DPro | LLys | LSer | NMe₂ | 1 |
| LAsn | LLys | LSer | NMe₂ | 1 |
| DSer | LLys | LSer | NMe₂ | 2 |
| LPro | LLys | LSer | NMe₂ | 1 |
| DAla | LLys | LSer | NMe₂ | 1 |
| LVal | DLys | DSer | NMe₂ | 1 |
| LAsn | DLys | DSer | NMe₂ | 1 |
| DPro | DLys | DSer | NMe₂ | 1 |
| DPro | DAsn | DSer | NMe₂ | 1 |
| LPro | DGln | DSer | NMe₂ | 1 |

TABLE 6

Library Yuan Chen. 0.2 copies used, about 8,000 beads pre-equilibrated with Cu(OAc)₂, for an assay done in 12DCE with 1.17 red beads found

| Hp1 | A₁ | A₂ | Hp2 | A₃ | A₄ |
|---|---|---|---|---|---|
| trans L | DPhe | LPro | cis L | DSer | DAla |
| trans L | DPro | LPhe | cis L | DSer | LPro |
| trans L | DPro | DSer | trans L | DSer | LPhe |
| trans L | DPhe | DAsn | trans L | DSer | LPro |
| trans L | DAla | LPro | cis L | DSer | DPro |
| trans L | LAsn | DPro | cis L | DSer | LAla |
| trans L | LPro | LPhe | cis L | DSer | LAla |
| trans L | DPro | LPhe | cis L | DSer | LPro |
| trans L | DSer | LAla | trans L | DSer | LPhe |
| trans L | DSer | LAsn | trans L | DSer | DPro |
| trans L | DAla | LAla | trans L | DSer | DSer |
| trans L | DAla | DPro | trans L | DSer | DSer |
| trans L | LAla | DPhe | trans L | DSer | LAla |
| cis L | DAla | DSer | trans L | DSer | DSer |
| cis L | LSer | DSer | trans D | DAla | DSer |
| trans D | LPro | DPro | cis L | DSer | DSer |

General Synthetic Procedures

All compounds were synthesized using standard laboratory techniques. Commercially available reagents and solvents were used without further purification. Reactions were monitored using thin-layer liquid chromatography (TLC) and visualization was done using UV light, cerium ammonium molybdate (CAM) and permanganate.

Nuclear magnetic resonance (NMR) spectra were recorded on a Varian VXR-400, Bruker 400 MHz or Bruker 300 MHz. Mass spectra were obtained with Jeol JMS-HX110A Mass Spectrometer and RIBERMAG R10-10 C. Gas chromatography was conducted with a HP 5890 GC equipped with an electron capture detector and HP ULTRA I fused silica capillary column. HPLC was directed with a Waters Millennium system, using a Nova Pak C18 column.

General Procedure for the Synthesis of Acid Fluorides:

To a 1 mmol solution of acid in 15 mL DCM at r.t. were added 1 eq. pyridine and 1.5 eq. cyanuric fluoride. The resulting solution was stirred under argon for 1.5 h. After dilution with 150 mL DCM, the organic layer was washed with 2 mL water. The solvent was removed to give the acid fluorides, which were used without further purification.

FIG. 11. Step (a) Synthesis of R(+)-2-(Trimethylsilyl) ethyl lactate. A solution of 460 μL (4.8 mmols) of R-methyl lactate, 1.6 mL (5.38 mmols) Ti(i-PrO)₄ and 820 μL (5.7 mmols) 2-(trimethylsilyl)ethanol in 30 mL dry THF was refluxed under argon overnight. Solvent was removed. Purification on column chromatography (DCM:acetone at 8:1) gave 700 mg of product in 85% yield.

$^1$H NMR (400 MHz, CDCl₃): δ4.28 (m, 2H), 4.22 (m, 1H), 2.82 (d, J=3.0 Hz, 1H), 1.41 (d, J=7.3 Hz, 3H), 1.02 (m, 2H), 0.05 (s, 9H). Chemical Impact Mass Spectrum (CIMS) (NH₃): M=190 calculated for $C_8H_{18}O_3$. Found m/z=191 (M+1).

FIG. 11. Steps (b, c). Synthesis of D—Ala—R(+)-2-(Trimethylsilyl)ethyl lactate. To a solution of 700 mg (3.68 mmols) D-LacTMSE in 15 mL DCM, were added 800 mg (4.2 mmols) of the acid fluoride of D—AlaBoc, 1.2 mL (7.4 mmols) N,N-diisopropylethylamine (DIEA) and a catalytic amount of dimethylaminopyridine (DMAP). The mixture was stirred at r.t. under argon for 3 h. Solvent was removed, and purification on column chromatography (DCM:Petroleum ether:EtOAc at 10:4:1) gave 900 mg of BocD—Ala—R(+)-2-(Trimethylsilyl)ethyl lactate (90% yield).

$^1$H NMR (400 MHz, CDCl₃): δ5.15–5.08 (m, 1H), 5.05–4.97 (bd, 1H), 4.42–4.37 (m, 1H), 4.27–4.19 (m, 2H), 1.51 (d, J=7.1 Hz, 3H) 1.47 (d, J=7.3 Hz, 3H), 1.45 (s, 9H) 1.05–0.96 (m, 2H), 0.05 (s, 9H). $^{13}$C NMR (300 MHz, CDCl₃): δ173.3, 170.9, 155.5, 80.3, 69.6, 64.3, 49.4, 28.7, 18.9, 17.7, 17.2, -1.1. CIMS (NH₃): M=361 calculated for $C_{16}H_{31}O_6NSi$. Found m/z=362 (M+1).

To this material were added 15 mL mixture DCM:TFA at 3:1, and the solution was stirred at r.t. for 15 min. After solvent removal, the TFA salt was used in the next step without further purification.

FIG. 11. Steps (f, g). A solution of 400 mg (1.26 mmols) Disperse Red 1, 232 mg (1.52 mmols) Methyl-(4-hydroxy) benzoate, 434 mg (1.76 mmols) PPh₃ and 400 μL (2.52 mmols) diethyl azodicarboxylate (DEAD) in 25 mL toluene/5 mL DCM, was stirred overnight under argon, at r.t. Solvent was removed. 200 mL DCM were added and the solution was washed with 3×15 mL 10% NaOH. Purification on column chromatography (DCM) gave the methyl ester as a red solid.

$^1$H NMR (400 MHz, CDCl₃): δ8.34 (d, J=9.1 Hz, 2H), 7.99 (d, J=8.8 Hz, 2H), 7.94 (d, J=9.0 Hz, 2H), 7.93 (d, J=9.1 Hz, 2H), 6.92 (d, J=8.8 Hz, 2H), 6.83 (d, J=9.0 Hz, 2H), 4.26 (t, J=5.9 Hz, 2H), 3.90 (t, J=5.9 Hz, 2H), 3.89 (s, 2H), 3.63 (q, J=7.1 Hz, 2H), 1.31 (t, J=7.1 Hz, 3H). CIMS (NH₃): M=448 calculated for $C_{24}H_{24}O_5N_4$. Found m/z=449 (M+1).

To this material were added 20 mL MeOH/40 mL THF/10 mL H₂O followed by 5 equivalents of LiOH, and the solution was refluxed for 3 h. Solvent removed. After addition of 200 mL DCM, HCl concentrated solution was slowly added until the solid has dissolved. The organic layer was washed with 2×10 mL water. Solvent was removed to give 475 mg product in 83% overall yield. This was used without further purification.

$^1$H NMR (400 MHz, dimethylsulfoxide-d₆ (DMSO)): δ8.37 (d, J=9.1 Hz, 2H), 7.94 (d, J=9.1 Hz, 2H), 7.87 (d, J=8.8 Hz, 2H), 7.85 (d, J=9.0 Hz, 2H), 7.05 (d, J=8.8 Hz, 2H), 6.97 (d, J=9.0 Hz, 2H), 4.28 (t, J=5.9 Hz, 2H), 3.92 (t, J=5.9 Hz, 2H), 3.63 (q, J=7.1 Hz, 2H), 1.20 (t, J=7.1 Hz, 3H). $^{13}$C NMR (300 MHz, DMSO): δ168.1, 162.4, 157.1, 152.5, 147.7, 143.7, 132.2, 126.9, 125.1, 123.4, 118.9, 114.9, 112.6, 66.6, 49.9, 46.2, 12.9. CIMS (NH$_3$): M=434 calculated for $C_{23}H_{22}O_5N_4$. Found m/z=435 (M+1).

FIG. 11. Step (h). To a solution of 265 mg (0.61 mmols) carboxylic acid in 10 mL DCM were added 53 μL (0.61 mmols) pyridine and 59 μL (0.8 mmols) cyanuric fluoride, and the mixture was stirred under argon at r.t. for 1.5 h. The solution was diluted with 150 mL DCM and washed 1×2 mL water. Solvent was removed to give the crude product.

FIG. 11. Step (d) Synthesis of DR1-PhNH—D—Ala—D-Lactate-2-(ethyl)trimethylsilyl. The acid fluoride obtained as above, was taken in 20 mL DCM and added to the TFA salt of the amine, followed by 190 μL (1.1 mmols) DIEA and a catalytic amount of DMAP, and the solution was stirred at r.t. under argon for 3 h. Solvent was removed and the product was purified by column chromatography (DCM:acetone at 15:1) to give 300 mg of red solid, in 80% yield.

$^1$H NMR (400 MHz, CDCl$_3$): δ8.33 (dd, J=8.0 Hz, J=1.9 Hz, 2H), 7.93 (dd, J=8.0 Hz, J=1.9 Hz, 2H), 7.92 (dd, J=8.0 Hz, J=2.1 Hz, 2H), 7.76 (dd, J=9.3 Hz, J=2.0 Hz, 2H), 6.92 (dd, J=8.0 Hz, J=2.1 Hz, 2H), 6.82 (dd, J=9.3 Hz, J=2.0 Hz, 2H), 6.59 (d, J=6.8 Hz, 1H), 5.20–5.11 (m, 1H), 4.90–4.82 (m, 1H), 4.28 (m, 4H), 3.90 (t, J=5.9 Hz, 2H), 3.62 (q, J=6.9 Hz, 2H), 1.61 (d, J=7.2 Hz, 3H), 1.54 (d, J=7.0 Hz, 3H), 1.29 (t, J=6.9 Hz, 3H), 1.05–0.99 (m, 2H), 0.05 (s, 9H). Low resolution mass spectrum (LRMS) fast atom bombardment (FAB): M=677 calculated for $C_{34}H_{43}O_8N_5Si$. Found m/z=678 (M+1).

FIG. 11. Step (e). Synthesis of depsipeptide analog DR1-PhNH—D—Ala—D-Lactic acid (1). To a solution of 300 mg (0.44 mmols) of trimethylsilylether (TMSE) protected 1 in 15 mL DMF, were added 440 μL (0.44 mmols) solution 1 M tetrabutylammonium fluoride (TBAF) in THF. Solution was stirred for 1 h at r.t. After solvent removal the solid was taken in 150 mL of EtOAc, acidified with acetic acid and washed with 3×10 mL water. The solvent was removed, and purification by gel chromatography (Sephadex LH-20) with MeOH (1% AcOH) gave 254 mg 1 as a red solid in 80% yield over the last two steps.

$^1$H NMR (400 MHz, CDCl$_3$): δ8.33 (dd, J=8.0 Hz, J=1.9 Hz, 2H), 7.93 (dd, J=8.0 Hz, J=1.9 Hz, 2H), 7.92 (dd, J=8.0 Hz, J=2.1 Hz, 2H), 7.76 (dd, J=9.3 Hz, J=2.0 Hz, 2H), 6.92 (dd, J=8.0 Hz, J=2.1 Hz, 2H), 6.82 (dd, J=9.3 Hz, J=2.0 Hz, 2H), 6.62 (d, J=6.8 Hz, 1H), 5.24–5.15 (m, 1H), 4.86–4.78 (m, 1H), 4.24 (t, J=5.9 Hz, 2H), 3.90 (t, J=5.9 Hz, 2H), 3.62 (q, J=6.9 Hz, 2H), 1.60 (d, J=7.2 Hz, 3H), 1.59 (d, J=7.0 Hz, 3H), 1.29 (t, J=6.9 Hz, 3H). $^{13}$C NMR (300 MHz, DMSO): 172.4, 171.6, 165.6, 160.7, 156.1, 151.5, 146.7, 142.7, 129.3, 125.9, 124.8, 122.4, 113.8, 111.6, 68.5, 65.5, 48.9, 47.9, 45.2, 16.6, 16.5, 11.9. High resolution mass spectrum (HRMS) (FAB): calculated for $C_{29}H_{31}O_8N_5$ (M+1) 578.2251, found 578.2255. Infrared analysis (IR) (polyethylene card): 3300, 3010, 2917, 2950, 1746, 1735, 1710, 1604, 1513, 1339, 1253.

Synthesis of 4-Nitro-PhNHD—Ala—D—Lac (5). To the TFA salt solution of D—Ala—D—LacTMSE in 10 mL DCM were added 2 equivalents of DIEA, a catalytic amount of DMAP and 1.3 equivalents of acid fluoride of the 4-nitrobenzoic acid dissolved in 10 mL DCM. The solution was stirred for 3 h at r.t. under argon. Solvent was removed and the product separated on silica gel column with DCM:hexanes:acetone at 7:2:1. Deprotection of the TMSE was performed as previously described, and after purification on Sephadex LH-20 (MeOH –1% AcOH), 5 was obtained as a white powder in 80% overall yield.

$^1$H NMR (400 MHz, DMSO): δ9.17 (d, J=6.8 Hz, 1H), 8.38 (d, J=7.9 Hz, 2H), 8.11 (d, J=7.9 Hz, 2H), 5.02–4.96 (m, 1H), 4.61–4.51 (m, 1H), 1.49 (d, J=7.3 Hz, 3H), 1.43 (d, J=7.0 Hz, 3H). $^{13}$C NMR (300 MHz, DMSO): δ172.8, 172.2, 165.7, 150.0, 140.1, 129.8, 124.4, 69.7, 49.1, 17.6, 17.3. HRMS (FAB): Calculated for $C_{13}H_{14}O_7N_2$ (M+1) 311.2713, found m/z=311.0887.

Synthesis of D—Ala derivative (4). The product was obtained as a white solid in the matter described above.

H$^1$ NMR (400 MHz, DMSO): δ12.68 (bs, 1H), 9.02 (d, J=7.1 Hz, 1H), 8.31 (d, J=8.7 Hz, 2H), 8.11 (d, J=8.7 Hz, 2H), 4.51–4.41 (m, 1H), 1.35 (d, J=7.3 Hz, 3H). C$^{13}$ NMR (300 MHz, DMSO): δ174.7, 165.4, 149.4, 140.4, 129.8, 124.4, 49.3, 17.6. CIMS (CH$_4$): M=238 calculated for $C_{10}H_{10}O_5N_2$. Found m/z=239 (M+1).

Synthesis of Peptide 4a.

BnNHL—Lys(Boc)NH$_2$: A solution of 470 mg (1 mmols) FmocL—Lys(Boc)OH, 230 mg (1.2 mmols) 1-ethyl-3-(3-dimethylaminopropyl)carbodiimide hydrochloride (EDC), 165 μL (1.5 mmols) benzylamine and a catalytic amount of DMAP in 25 mL DCM, was stirred at r.t. under argon for 2 h. After dilution with 25 mL DCM, the solution was washed with 5 mL solution HCl 1 M. Solvent was removed to give the benzylamide as a white solid. This was deprotected by stirring with 50 mL solution DCM:piperidine at 4:1, at r.t. for 30 min. Separation on silica gel column with DCM:MeOH at 15:1 to 7:1, gave the amine in 90% yield (300 mg).

$^1$H NMR (400 MHz, CDCl$_3$): δ7.71–7.59 (bt, 1H), 7.38–7.27 (m, 5H), 4.63–4.53 (bt, 1H), 4.48 (d, J=5.9 Hz, 2H), 3.45–3.37 (m, 1H), 3.18–3.04 (m, 2H), 1.94–1.82 (m, 1H), 1.68–1.41 (m, 5H), 1.42 (s, 9H). CIMS (NH$_3$): M=335 calculated for $C_{18}H_{29}O_3N_3$. Found m/z=336 (M+1).

BnNHL—Lys(Boc)—D—ProNH: To the solution of amine were added 340 mg (1 mmols) acid fluoride of FmocD—Pro and 350 μL (2 mmols) DIEA in 50 mL DCM, and stirred at r.t. under argon for 1 h. After solvent removal, purification was completed on silica gel column with DCM:acetone at 5:2. Fmoc deprotection was carried out as above. After separation on silica gel column with DCM:MeOH at 10:1 then 7:1 (1% TEA), the amine was obtained in 85% yield over the two steps.

$^1$H NMR (300 MHz, CDCl$_3$): δ8.03 (d, J=8.3 Hz, 1H), 7.39–7.23 (m, 5H), 6.91–6.82 (m, 1H), 4.67–4.59 (bt, 1H), 4.57–4.31 (m, 3H), 3.81–3.72 (m, 1H), 3.17–3.04 (m, 2H), 3.02–2.74 (m, 2H), 2.18–1.41 (m, 10H), 1.42 (s, 9H). CIMS (NH$_3$): M=432 calculated for $C_{23}H_{36}O_4N_4$. Found m/z=433 (M+1).

BnNHL—Lys(Boc)—D—Pro—L—Ser(tBut)NH$_2$: To the above amine in 50 mL DCM were added 380 mg (1 mmols) acid fluoride of FmocL—Ser(tBut) and 350 μL (2 mmols) DIEA, and the resulting solution was stirred under argon for 1 h. After solvent removal, the purification was achieved by flash chromatography with DCM:acetone at 2:1. After Fmoc deprotection and separation on silica gel column with DCM:MeOH at 14:1, the amine was obtained as 420 mg of white solid in 75% yield.

$^1$H NMR (300 MHz, CDCl$_3$): δ7.66–7.58 (bt, 1H), 7.39–7.23 (m, 5H), 6.82 (d, J=8.3 Hz, 1H), 4.79–4.71 (bt, 1H), 4.71–4.27 (m, 4H), 3.88–3.71 (m, 1H), 3.65–3.13 (m, 6H), 2.31–1.46 (m, 10H), 1.46 (s, 9H), 1.15 (s, 9H). CIMS (NH$_3$): M=575 calculated for $C_{30}H_{49}O_6N_5$. Found m/z=576 (M+1).

BnNHL—Lys(Boc)—D—Pro—L—Ser(tBut)CONMe$_2$: Capping of the serine was accomplished with excess dimethylcarbamyl chloride and DIEA, by stirring the solution with a catalytic amount of DMAP under argon for 3 h at r.t. Purification on a silica gel column with DCM:acetone at 1:1, gave the peptide in 85% yield.

$^1$H NMR (300 MHz, CDCl$_3$): δ7.46 (d, J=8.3 Hz, 1H), 7.34–7.24 (m, 5H), 5.43–5.32 (bt, 1H), 5.12–5.02 (bt, 1H), 3.74–3.56 (m, 4H), 3.18–3.06 (m, 2H), 2.84 (s, 6H), 2.38–1.45 (m, 10H), 1.46 (s, 9H), 1.17 (s, 9H). $^{13}$C NMR (300 MHz, CDCl$_3$): δ172.3, 139.1, 128.9, 127.9, 127.6, 79.5, 74.2, 62.2, 61.1, 54.1, 47.8, 43.6, 40.4, 36.5, 30.9, 29.5, 29.3, 28.9, 27.8, 24.6, 22.9. CIMS (NH$_3$): M=646 calculated for C$_{33}$H$_{54}$O$_6$N$_7$. Found m/z=647 (M+1).

BnNHL—Lys—D—Pro—L—Ser(tBut)CONMe$_2$ (7): The Boc was selectively removed by stirring the peptide in DCM:TFA at 3:1 for 30 min at r.t. After the excess TFA was eliminated, the peptide was purified by gel filtration on Sephadex LH-20 with DMF.

$^1$H NMR (400 MHz, DMSO): δ8.28 (t, J=5.8 Hz, 1H), 7.82 (d, J=8.2 Hz, 1H), 7.65 (bs, 3H), 7.32–7.18 (m, 5H), 6.22 (d, J=6.3 Hz, 1H), 4.42–4.12 (m, 5H), 3.74–3.36 (m, 4H), 2.72 (s, 6H), 2.08–1.16 (m, 10H), 1.12 (s, 9H). LRMS (FAB): M=546 calculated for C$_{33}$H$_{46}$O$_5$N$_6$. Found m/z=547 (M+1).

BnNHL—Lys—D—Pro—L—SerCONMe$_2$ (4a): To the Boc protected peptide in 10 mL DCM stirred under argon at 0° C., were added 1.3 equivalents of TiCl$_4$ solution 1 M in DCM. The solution was stirred for 15 min, after which 5 mL saturated aqueous NaHCO$_3$ solution were added. The organic layer was removed, and the water evaporated under high vacuum. To the solid obtained were added 25 mL MeOH and the solids were filtered off. Further purification was accomplished by gel chromatography Sephadex LH-20 using MeOH as eluent, to give the peptide as a white solid.

$^1$H NMR (400 MHz, DMSO): δ8.28 (bt, 1H), 7.74 (d, J=8.2 Hz, 1H), 7.33–7.18 (m, 5H), 6.6 (bs, 1H), 6.24–6.14 (m, 1H), 5.02–4.90 (m, 2H), 4.39–4.17 (m, 5H), 3.85–3.49 (m, 4H), 2.90–2.82 (m, 2H), 2.77 (s, 6H), 2.08–1.22 (m, 10H). $^{13}$C NMR (300 MHz, DMSO): δ172.4, 172.2, 158.9, 140.4, 129.1, 128.0, 127.7, 127.5, 63.1, 60.9, 55.8, 53.8, 47.7, 42.8, 36.7, 31.8, 30.1, 24.8, 23.3. LRMS (FAB): M=490 calculated for C$_{24}$H$_{38}$O$_5$N$_6$. Found m/z=491 (M+1).

Synthesis of Control Peptides (6) and (8)

BnNHD—ProBoc: To 500 mg (2.32 mmols) of BocProOH in 15 mL of DCM were added 187 μL (2.32 mmols) pyridine and 324 μL (3.48 mmols) cyanuric fluoride. The resulting solution was stirred under argon at r.t. for 1 h. After dilution with DCM to 150 mL, the organic layer was washed with 2 mL water. Solvent was removed, and to this crude material 253 μL (2.3 mmols) benzylamine and 800 μL (4.6 mmols) DIEA were added in 20 mL DCM. The solution was stirred at r.t. under argon for 1.5 h. Solvent was removed and after purification by silica gel column chromatography (DCM:acetone at 10:1), the peptide was obtained as 670 mg of white solid in 96% yield.

$^1$H NMR (400 MHz, CD$_3$OD): δ7.27–7.37 (m, 4H), 7.20–7.29 (m, 1H), 4.43–4.46 (m, 1H), 4.27–4.31 (m, 1H), 4.13–4.22 (m, 1H), 3.50–3.58 (m, 1H), 3.38–3.46 (m, 3H), 2.18–2.31 (m, 1H), 1.81–2.02 (m, 3H), 1.47 (s, 3H), 1.33 (s, 6H). CIMS (NH$_3$): M=305 calculated for C$_{17}$H$_{24}$O$_3$N$_2$. Found m/z=306 (M+1).

BnNHD—Pro—L—Ser(tBut)Fmoc: To 304 mg (1 mmol) of BnNH—L—ProBoc were added 100 mL DCM:TFA at 4:1, and the solution was stirred at r.t. for 1 h. The excess TFA was removed, and to a solution of this crude material in 25 mL DCM were added 400 mg (1.04 mmols) of the acid fluoride of FmocL—Ser(OtBut) and 2 eq. of DIEA. After stirring at r.t. for 45 min., the solvent was removed and the peptide was purified by column chromatography (DCM:acetone at 9:1) to give 550 mg of a white foam in 97% yield. CIMS (NH$_3$) M=569 calculated for C$_{34}$H$_{39}$O$_5$N$_3$. Found m/z=570 (M+1).

BnNHD—Pro—L—Ser(tBut)NH$_2$: Deprotection of the Fmoc group was achieved by stirring the substrate in a solution of DCM:Piperidine at 4:1 for 30 min. Solvent was removed, and purification of the crude by flash chromatography with DCM:MeOH at 8:1, gave 315 mg amine in 94% yield. CIMS (NH$_3$): M=347 calculated for C$_{19}$H$_{29}$O$_3$N$_3$. Found m/z=348 (M+1).

BnNHD—Pro—L—Ser(tBut)NHCONMe$_2$: To the solution of amine in 10 mL DCM, DIEA and dimethylcarbamyl chloride were added in excess over a period of 5–7 h, until the TLC does not indicate the presence of the amine. Solvent was removed. Purification on a silica gel column with DCM:acetone at 1:1 gave 300 mg product in 80% yield.

$^1$H NMR (400 MHz, CDCl$_3$): δ7.98 (t, J=6.1 Hz, 1H), 7.28–7.15 (m, 5H), 5.15 (d, J=6.1 Hz, 1H), 4.72–4.25 (m, 4H), 4.06–3.55 (m, 4H), 2.59 (s, 6H), 2.35–1.92 (m, 4H), 1.17 (s, 9H). CIMS (NH$_3$): M=418 calculated for C$_{22}$H$_{34}$O$_4$N$_4$. Found m/z=419 (M+1).

BnNHD—Pro—L—Ser(OH)NHCONMe$_2$ (6): Deprotection of the t-Butyl group was accomplished by stirring the peptide with a solution of DCM:TFA at 4:1 for 1 h at r.t. Solvent was removed, and after purification by silica gel column chromatography (DCM:acetone:MeOH at 5:5:1), the product was obtained as 110 mg of oil in 42% yield (87% yield based on recovered starting material). Longer reaction time or more TFA led to decomposition of starting material. Further purification was done by size-exclusion chromatography on Sephadex LH-20 with MeOH. Recrystallization from DCM/hexane gave 100 mg of a white solid.

$^1$H NMR (400 MHz, DMSO): δ8.24 (t, J=6.1 Hz, 1H), 7.35–7.17 (m, 5H), 6.38 (d, J=6.1 Hz, 1H), 4.72–4.25 (m, 4H), 4.06–3.55 (m, 4H), 2.59 (s, 6H), 2.35–1.92 (m, 4H), 1.17 (s, 9H). $^{13}$C NMR (300 MHz, CDCl$_3$): δ171.11, 170.89, 157.37, 137.78, 128.04, 126.92, 126.75, 64.08, 59.94, 53.21, 47.11, 42.84, 35.66, 28.36, 24.27. HRMS (FAB): calculated for C$_{18}$H$_{26}$O$_4$N$_4$ (M+1) 363.2032, found 363.2019. IR (polyethylene card): 3307, 2918, 2849, 1659, 1651, 1643, 1634, 1538, 1472, 1462, 1231, 1065.

BnNHL—LysNHAc (8): To 250 mg (0.74 mmols) of the benzylamide of L—Lys (δNHBoc) in 20 mL DCM were added 200 mL TEA, 200 mL Ac$_2$O and a catalytic amount of DMAP. After stirring the mixture at r.t. for 1 h, the solvent was removed and purification was performed on a silica gel column with DCM:acetone at 1:1. After standard deprotection of Boc and removal of the excess TFA, 10 mL saturated NaHCO$_3$ were added and the free amine extracted several times with DCM. Further purification was achieved on a Sephadex LH-20 column with MeOH.

$^1$H NMR (300 MHz, DMSO): δ8.55 (t, J=6.0 Hz, 1H), 8.11 (d, J=8.0 Hz, 1H), 7.32–7.18 (m, 5H), 4.28–4.12 (m, 3H), 2.52–2.42 (m, 2H), 1.82 (s, 3H), 1.66–1.16 (m, 6H). $^{13}$C NMR (300 MHz, DMSO): δ173.4, 172.5, 138.9, 128.5, 127.5, 127.2, 53.9, 43.0, 39.9, 31.6, 28.5, 23.0, 21.5. CIMS (CH$_4$): M=277 calculated for C$_{15}$H$_{23}$O$_2$N$_3$. Found m/z=278 (M+1).

Figure 12:
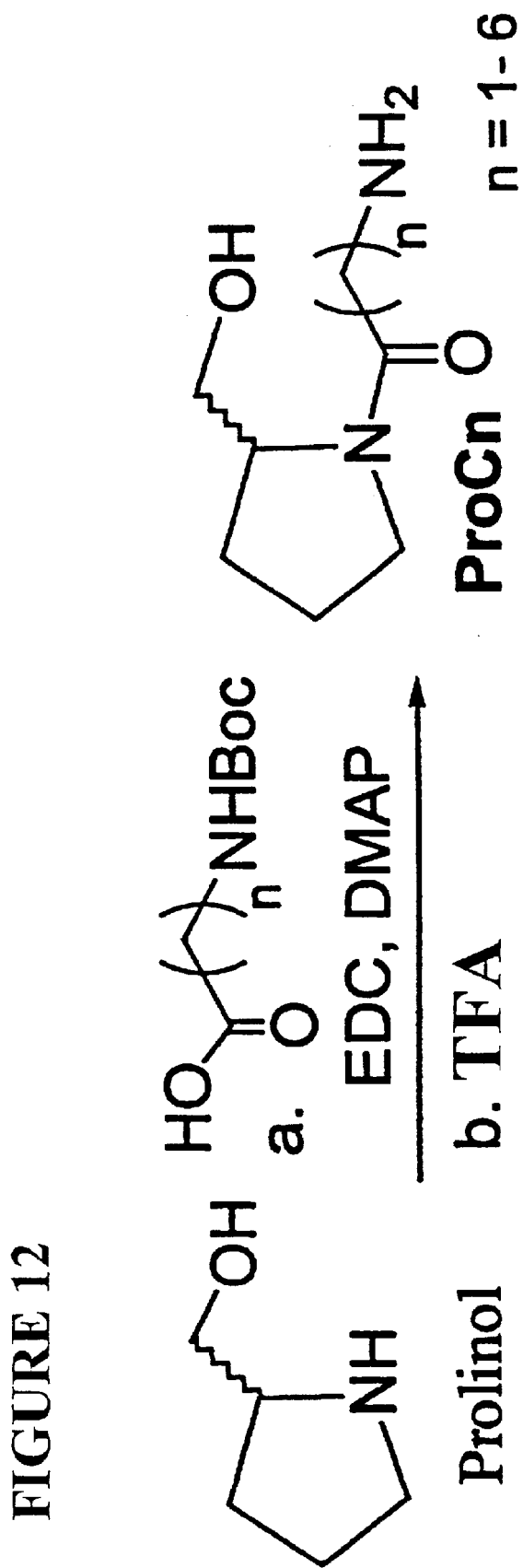
FIG. 12. General procedure for the synthesis of compounds ProCn.

To 0.5 mmols prolinol in 25 mL DCM were added 1.2 equivalents Boc protected aminoacid, 1.2 equivalents EDC and a catalytic amount of DMAP (FIG. 12). After stirring the mixture at r.t. for 2 h, 100 mL of DCM were added and the solution was washed with 5 mL HCl 1 N. Solvent was removed and the product purified on silica gel column with DCM:acetone at 1:1 to give a colorless oil in yields higher than 90%.

SProC1NHBoc: $^1$H NMR (400 MHz, CDCl$_3$): δ5.48 (bt, 1H), 4.57 (d, J=6.1 Hz, 1H), 4.28–4.18 (m, 1H), 4.02–3.78 (m, 2H), 3.74–3.40 (m, 4H), 2.12–1.78 (m, 3H), 1.67–1.62 (m, 1H), 1.47 (s, 9H). CIMS (CH$_4$): M=258 calculated for C$_{12}$H$_{22}$O$_4$N$_2$. Found m/z=259 (M+1).

SProC2NHBoc: $^1$H NMR (400 MHz, CDCl$_3$): δ5.28 (bt, 1H), 4.98 (bd, 1H), 4.28–4.18 (m, 1H), 3.74–3.54 (m, 2H), 3.51–3.42 (m, 4H), 2.54 (t, J=7.3 Hz, 2H), 2.15–1.87 (m, 3H), 1.68–1.55 (m, 1H), 1.45 (s, 9H). CIMS (NH$_3$): M=272 calculated for C$_{13}$H$_{24}$O$_4$N$_2$. Found m/z=273 (M+1).

SProC3NHBoc: $^1$H NMR (400 MHz, CDCl$_3$): δ4.96 (bd, 1H), 4.75 (bt, 1H), 4.28–4.18 (m, 1H), 3.82–3.74 (m, 2H), 3.62–3.47 (m, 3H), 3.24–3.12 (m, 2H), 2.42–2.34 (m, 2H), 2.10–1.71 (m, 3H) 1.68–1.58 (m, 1H), 1.48 (s, 9H). $^{13}$C NMR (300 MHz, CDCl$_3$): δ174.0, 156.7, 79.6, 67.4, 61.4, 48.5, 40.3, 32.4, 28.8, 28.6, 25.4, 24.8. CIMS (NH$_3$): M=286 calculated for C$_{14}$H$_{26}$O$_4$N$_2$. Found m/z=287 (M+1).

SProC4NHBoc: $^1$H NMR (400 MHz, CDCl$_3$): δ5.11 (bd, 1H), 4.65 (bt, 1H), 4.28–4.20 (m, 1H), 3.72–3.47 (m, 4H), 3.22–3.11 (m, 2H), 2.37 (t, 2H, J=7.3 Hz), 2.13–1.81 (m, 3H), 1.74–1.52 (m, 4H), 1.47 (s, 9H). $^{13}$C NMR (300 MHz, CDCl$_3$): δ174.6, 156.5, 79.5, 68.0, 61.6, 48.5, 40.5, 34.8, 29.9, 28.8, 28.7, 24.8, 22.1. CIMS (NH$_3$): M=300 calculated for C$_{15}$H$_{28}$O$_4$N$_2$. Found m/z=301 (M+1).

SProC5NHBoc: $^1$H NMR (400 MHz, CDCl$_3$): δ5.14 (d, J=6.0 Hz, 1H), 4.54 (bt, 1H), 4.28–4.20 (m, 1H), 3.72–3.45 (m, 4H), 3.18–3.07 (m, 2H), 2.73 (t, J=7.3 Hz, 2H), 2.12–1.72 (m, 3H), 1.74–1.42 (m, 7H), 1.47 (s, 9H). $^{13}$C NMR (300 MHz, CDCl$_3$): δ174.7, 156.7, 79.4, 67.7, 61.5, 48.5, 40.7, 35.3, 30.3, 28.8, 28.6, 26.9, 24.7. CIMS (NH$_3$): M=314 calculated for C$_{16}$H$_{30}$O$_4$N$_2$. Found m/z=315 (M+1).

SProC6NHBoc: H$^1$ NMR (400 MHz, CDCl$_3$): δ5.28 (d, J=6.0 Hz, 1H), 4.52 (bt, 1H), 4.29–4.21 (m, 1H), 3.74–3.42 (m, 4H), 3.18–3.07 (m, 1H), 2.72 (t, J=7.3 Hz, 2H), 2.22–1.84 (m, 3H), 1.72–1.34 (m, 9H), 1.47 (s, 9H). $^{13}$C NMR (300 MHz, CDCl$_3$): δ174.7, 154.2, 68.2, 61.6, 48.5, 35.4, 30.3, 29.4, 28.8, 28.7, 26.9, 25.0, 24.8. CIMS (NH$_3$): M=228 calculated for C$_{17}$H$_{32}$O$_4$N$_2$. Found m/z=229 (M+1).

Deprotection of Boc was achieved with TFA:DCM at 1:3 in 30 min. After the excess TFA was removed on high vacuum, the salt was dissolved in 1 mL water and added to a small Dowex 50W×4–400 ion exchange column, and eluted with a solution of NH$_4$OH 1 M. Further purification was achieved using a C18 cartridge (Waters), eluting with water. The amine was obtained in 80% overall, as a colorless oil.

SProC1: $^1$H NMR (400 MHz, DMSO): δ3.96–3.78 (m, 1H), 3.53–3.15 (m, 6H), 1.94–1.72 (m, 4H). $^{13}$C NMR (300 MHz, DMSO): δ172.4, 63.3, 61.9, 59.6, 58.6, 46.2, 44.5, 28.7, 27.3, 24.2, 21.9. CIMS (NH$_3$): M=158 calculated for C$_7$H$_{14}$O$_2$N$_2$. Found m/z=159 (M+1).

SProC2: $^1$H NMR (400 MHz, DMSO): δ4.01–3.85 (m, 1H), 3.52–3.08 (m, 6H), 2.52–2.34 (m, 2H), 1.98–1.77 (m, 4H). $^{13}$C NMR (300 MHz, DMSO): δ171.2, 63.3, 62.1, 59.4, 59.3, 47.7, 46.1, 28.6, 27.6, 24.3, 22.2. CIMS (NH$_3$): M=172 calculated for C$_8$H$_{16}$O$_2$N$_2$. Found m/z=173 (M+1).

SProC3: $^1$H NMR (400 MHz, DMSO): δ3.95–3.87 (m, 1H), 3.54–3.20 (m, 5H), 2.94 (bt, 2H), 2.94–2.72 (m, 2H) 1.96–1.52 (m, 6H). $^{13}$C NMR (300 MHz, DMSO): δ171.9, 63.3, 62.1, 59.3, 59.1, 47.6, 46.1, 32.3, 31.7, 28.6, 27.6, 24.3, 22.2. CIMS (NH$_3$): M=186 calculated for C$_9$H$_{18}$O$_2$N$_2$. Found m/z=187 (M+1).

SProC4: $^1$H NMR (400 MHz, DMSO): δ3.95–3.85 (m, 1H), 3.49–3.09 (m, 4H), 2.94–2.48 (m, 2H) 2.37–2.12 (m, 2H), 1.96–1.34 (m, 8H). $^{13}$C NMR (300 MHz, DMSO): δ171.9, 63.3, 62.1, 59.4, 59.3, 47.6, 46.1, 42.1, 34.6, 33.9, 32.3, 28.6, 27.5, 24.3, 22.9, 22.6, 22.1, 21.6. CIMS (NH$_3$): M=200 calculated for C$_{10}$H$_{20}$O$_2$N$_2$. Found m/z=201 (M+1).

SProC5: $^1$H NMR (400 MHz, DMSO): δ3.88–3.74 (m, 1H), 3.52–3.22 (m, 4H), 2.91–2.52 (m, 2H), 2.39–2.19 (m, 2H) 1.95–1.74 (m, 4H), 1.54–1.22 (m, 6H). $^{13}$C NMR (300 MHz, DMSO): δ171.9, 63.4, 62.2, 59.4, 59.3, 47.6, 46.1, 34.8, 34.1, 28.6, 27.5, 26.9, 25.6, 24.9, 24.3, 22.1. HRMS (FAB): calculated for C$_{11}$H$_{22}$O$_2$N$_2$ 214.3079. Found 214.1619.

RProC5: $^{13}$C NMR (300 MHz, DMSO): δ171.8, 63.3, 62.1, 59.4, 59.3, 47.6, 46.1, 34.6, 33.9, 29.0, 28.6, 27.5, 26.5, 25.3, 24.7, 24.3, 22.1. CIMS (NH$_3$): M=214 calculated for C$_{11}$H$_{22}$O$_2$N$_2$. Found m/z=215 (M+1).

SProC6: $^1$H NMR (400 MHz, DMSO): δ4.01–3.70 (m, 1H), 3.52–3.18 (m, 4H), 2.93–2.48 (m, 2H), 2.39–2.14 (m, 2H) 1.95–1.68 (m, 4H), 1.54–1.18 (m, 8H). $^{13}$C NMR (300 MHz, DMSO): δ172.0, 63.3, 62.1, 59.4, 47.6, 46.1, 34.8, 34.1, 29.5, 28.6, 27.5, 27.1, 25.8, 25.2, 24.3, 22.1. CIMS (NH$_3$): M=228 calculated for C$_{12}$H$_{24}$O$_2$N$_2$. Found m/z=229 (M+1).

Preparation of in vivo Study Samples

For the in vivo experiments, deprotection of the S,RProCnNHBoc derivatives was performed by stirring for 1 h in 3 M HCl in EtOAc. Solvent was removed and the oils were extensively dried on high vacuum. 100 mM stock solutions of each derivative were made in sterile PBS pH 7.4 and the pH of the resulting solutions was adjusted with concentrated NaOH to 7.

Figure 13:
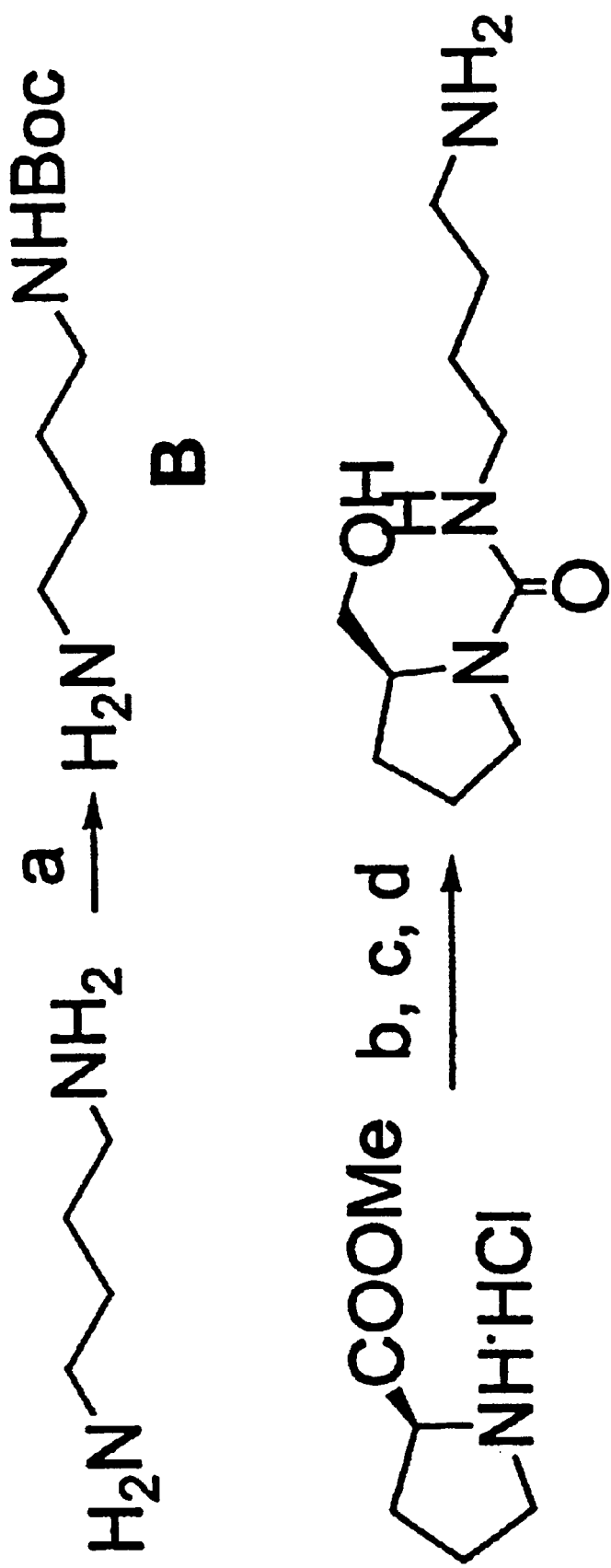
FIG. 13. Synthesis of SProUC4. (a) BocON, TEA; (b) phosgene, B, pyridine; (c) NaBH$_4$; (d) TFA.

FIG. 13. Step (a). To 1 mL (9.9 mmols) diamine in 100 mL DCM were added 2.45 g (9.9 mmols) BocON and 1.4 mL TEA, and the solution was stirred at r.t. overnight. The product was purified on silica gel column with DCM:MeOH at 1:1 (5% TEA) to give 1.8 g of white solid in 96% yield.

$^1$H NMR (400 MHz, CDCl$_3$): δ4.68 (bt, 1H), 3.18 (bq, 2H), 2.72 (t, J=6.7 Hz, 2H), 1.60–1.50 (m, 2H), 1.52 (s, 9H), 1.31–1.21 (m, 2H).

FIG. 13. Step (b). To 83 mg (0.5 mmols) of L—ProOMe.HCl were added 100 μL TEA followed by 1 mL solution 2 M of phosgene in toluene, and the mixture was stirred at r.t. for 1 h. After a careful removal of excess phosgene, the product was dissolved in 5 mL DCM and added to a solution of 140 μL (1.3 mmols) pyridine and 94 mg (0.5 mmols) amine in 15 mL DCM. The solution was stirred at r.t. for 2 h. Solvent removal, followed by purification on silica gel column with DCM:acetone at 1:1 gave 150 mg of product as a colorless oil, in 90% yield.

$^1$H NMR (400 MHz, CDCl$_3$): δ4.67–4.58 (m, 1H), 4.57–4.51 (m, 1H), 4.47–4.41 (m, 1H), 3.74 (s, 3H), 3.52–3.22 (m, 4H), 3.19–3.08 (m, 2H), 2.17–1.97 (m, 4H), 1.60–1.50 (m, 4H), 1.48 (s, 9H). CIMS (NH$_3$): M=343 calculated for C$_{16}$H$_{29}$O$_5$N$_3$. Found m/z=344 (M+1).

FIG. 13. Step (c). To the methyl ester were added 166 mg (10 eq.) NaBH$_4$ in 15 mL MeOH and the solution was stirred at r.t. for 20 min and then refluxed for 2 h. Purification on silica gel column with DCM:acetone at 1:1 gave the product quantitatively as a colorless oil.

$^1$H NMR (400 MHz, CDCl$_3$): δ5.18 (bd, 1H), 4.86 (bd, 1H), 4.65 (bt, 1H), 4.17–4.05 (m, 1H), 3.72–3.52 (m, 2H), 3.40–3.11 (m, 6H), 2.11–1.87 (m, 2H), 1.62–1.57 (m, 4H), 1.48 (s, 9H). $^{13}$C NMR (300 MHz, CDCl$_3$): δ159.6, 156.7, 79.5, 68.0, 60.6, 47.2, 40.7, 40.6, 29.0, 28.8, 27.8, 27.7, 24.5. CIMS (NH$_3$): M=315 calculated for C$_{15}$H$_{29}$O$_4$N$_3$. Found m/z=316 (M+1).

FIG. 13. Step (d). Deprotection of the Boc group and work up of the resulting amine, were completed as described for ProCn.

$^1$H NMR (400 MHz, DMSO): δ6.37 (bt, 1H), 3.71–3.63 (m, 1H), 3.44–3.18 (m, 4H), 3.12–2.90 (m, 2H), 2.73 (bt, 2H), 1.88–1.68 (m, 4H), 1.55–1.35 (m, 2H). $^{13}$C NMR (300

MHz, DMSO): δ158.4, 64.5, 59.5, 47.0, 28.4, 27.9, 24.1. CIMS (CH$_4$): M=215 calculated for C$_{10}$H$_{21}$O$_2$N$_3$. Found m/z=216 (M+1).

In vitro Hydrolysis of D—Ala—D—Lac

Figure 14:
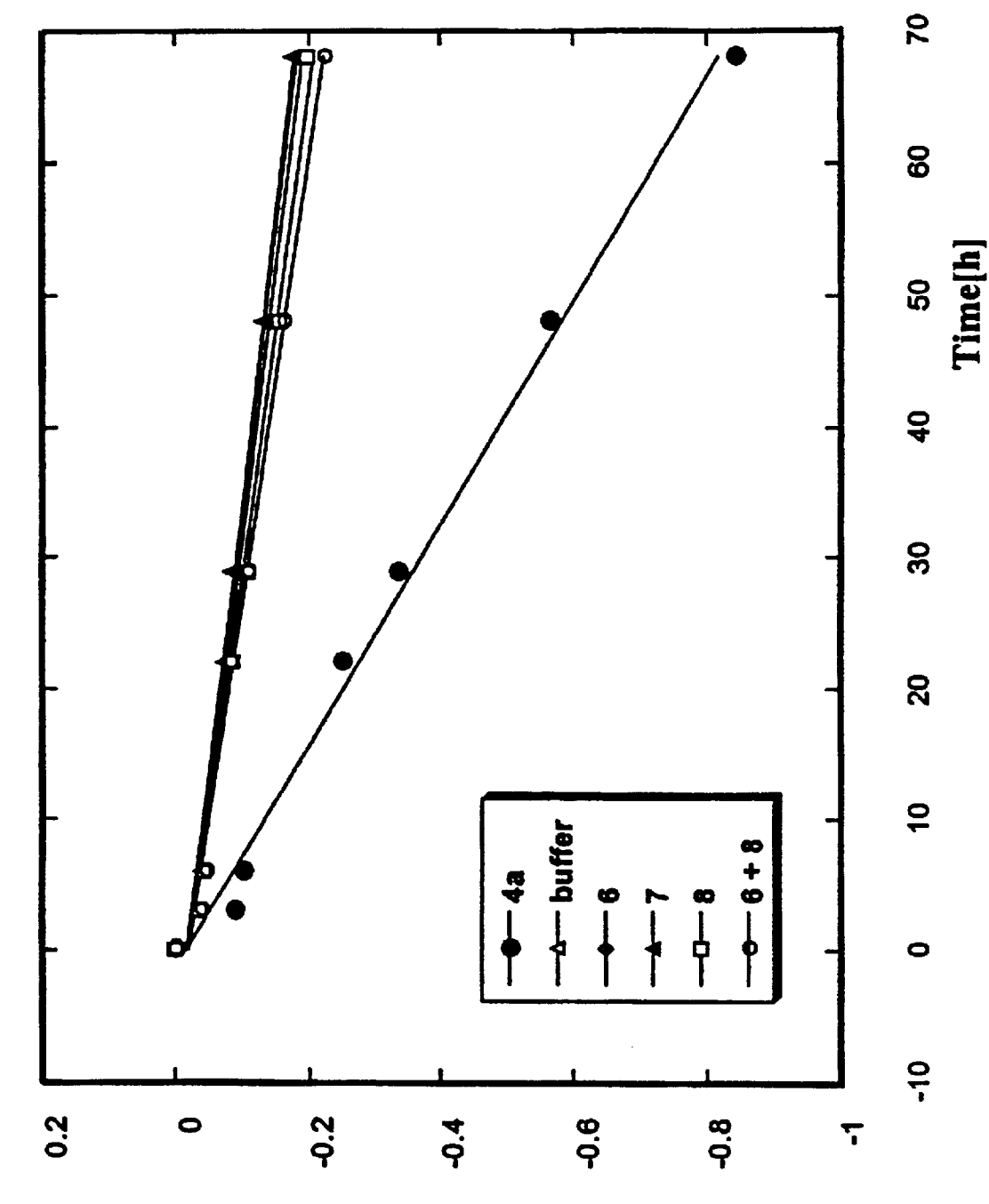
FIG. 14. Representative kinetic data for the hydrolysis of depsipeptide derivative 5 by 20 mM phosphate buffer (pH 7.0) (triangles), BnNHL—Lys—D—Pro—L—Ser dimethylurea 4a (filled circle), control sequence 6 (diamond), control sequence 7 (filled triangle), control sequence 8 (box), control sequences 6+8 (circle). Assays were performed with depsipeptide derivative 5 at 0.5 mM, while peptides were run at 12 mM. The graph is the average of five separate runs.

The ability of peptide 4a in cleaving the substrate 5 was assessed in aqueous phosphate buffer pH 7 at 37° C. Using HPLC and monitoring the p-NO$_2$-phenyl derivative by UV at 275 nm, we could easily follow the disappearance of D—Ala—D—Lac derivative 5 and the formation of the hydrolyzed product 4. No significant effect on the rate of hydrolysis over buffer was observed using the control sequences 6, 7, 8 alone or 6 and 8 combined (FIG. 14). A 20% hydrolysis of D—Ala—D—Lac in the presence of 4a was observed after 24 h.

The prolinol derivatives were additionally, tested for their ability to cleave 5 in aqueous phosphate buffer pH 7.0 at 37° C. A 50% D—Ala—D—Lac hydrolysis was observed after 24 h implying that the SProC5 derivative is twice as active as the initial peptide 4a. Activity declines in the SProCn series with the decrease of the chain length from 5 carbons to 1 carbon. This result can be explained not only by a decrease in efficiency of the terminal amino in reaching to the carboxylate and ester of D—Ala—D—Lac with the shortening of the chain, but also by the decrease in nucleophilicity of the hydroxyl. A 6 carbon chain is also less active. The lower activity of SProC6 is probably due to the higher flexibility of the carbon chain that does not render the amino group available for the reaction.

To confirm these speculations we compared the chemical shifts of the OH and NH in the H$^1$ NMR spectra of the NHBoc protected SProCn series (Table 7). The study shows that there is a competition between the amino group and the hydroxyl for hydrogen bonding to the amide. With the decrease of the chain length, the probability of the OH being hydrogen bonded decreases substantially, fact reflected in the chemical shifts of the OH and NH with the change in the length of the carbon chain.

TABLE 7

Shifts in the NMR position of OH and NHBoc (Boc-protected small molecule series) with the modification of the carbon chain length.

| Boc-derivative | OH position (ppm) | NH position (ppm) |
|---|---|---|
| SProC1 | 4.57 | 5.48 |
| SProC2 | 4.98 | 5.28 |
| SProC3 | 4.96 | 4.75 |
| SProC4 | 5.11 | 4.65 |
| SProC5 | 5.14 | 4.54 |
| SProC6 | 5.28 | 4.52 |
| SProUC4 | 4.86 | 4.65 |

The table also explains the low activity of SProUC4, derivative in which the amide is replaced by urea. The urea is a better acceptor than the amide and should increase the reactivity of the hydroxyl. However, it is possible that structural constraints imposed by the urea play an important role and do not allow for proper orientation for H-bonding.

Mechanistic Studies

To get insights on the mechanism of this reaction, the cleavage of 1 by 4a was studied in THF-5% water. Stock solutions of 2 mM concentration of 1 in THF and 49 mM of 4a (lyophilized from PIPES buffer pH 7.0) in water were prepared. In three ampoules were added 40 μL solution of 1, 7 μL of 4a and the volume was adjusted to 160 μL with THF. For background measurements, in another three ampoules 7 μL water were added instead of 4a to the solution of 1. All six ampoules were sealed under an argon stream and placed in an oil bath heated at 60° C. For each measurement one vial was opened and 5 μL were taken, diluted with 5 μL THF and 2 μL of this solution were injected in the HPLC.

The reaction proceeds with the formation of a transesterification product 3, which then is cleaved by water (Scheme 3).

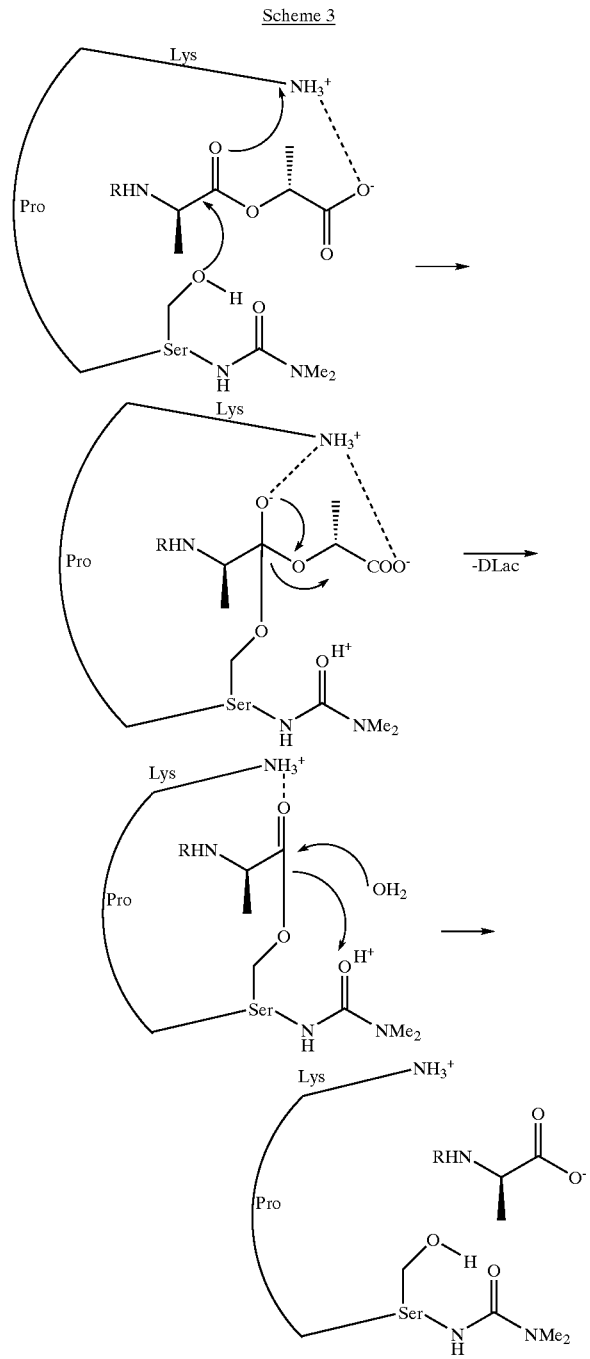

Scheme 3

The reaction could be monitored by HPLC at 485 nm, and the separation of the three components was easily performed on an analytical reverse phase column using a gradient of acetonitrile:water. Isolation of the intermediate 3 proved to be however, more difficult. Application of the assay mixture to a size exclusion column (Sephadex LH-20 with DMF) gave a fraction enriched in 3, and this was used for a COSY-$^1$H NMR analysis (FIG. 17). Comparison of the NMR spectra of 4a, 3 and 9 (FIG. 16) confirmed the identity of the intermediate 3. Mass spectrum analysis (MS) was used to additionally establish the identity of the three peaks seen in the HPLC chromatogram (FIG. 15). The above description is for the purposes of teaching the person of ordinary skill in the art how to practice the invention, and is not intended to detail all those obvious modifications and variations of it, which will become apparent to the skilled worker upon reading the description. It is intended, however, that all such obvious modifications and variations be included within the scope of the present invention, which is defined by the following claims.

References

1. E. P. Abraham, E Chain, *Nature* 146, 837 (1940).
2. T. G. Emori, R. P. Gaynes, *Clin. Microbiol. Rev.* 6, 428 (1993).
3. N. Woodford, *J. Med. Microbiol.* 47, 849 (1998).
4. T. M. Perl, *Am. J. Med.* 106:5A, 26S (1999).
5. G. L. French, *Clin. Infect. Dis.* Suppl 1, S75 (1998).
6. P. E. Reynolds, *Eur. J. Microbiol. Infect. Dis.* 8, 943 (1989).
7. G. D. Wright, C. T. Walsh, *Acc. Chem. Res.* 25, 468 (1992).
8. C. T. Walsh, *Science* 261, 308 (1993).
9. B. L. M. De Jonge, S. Handwerger, D. Gage, *Microb. Drug Resist.* 2, 225 (1996).
10. S. Evers, R. Quintiliani Jr, P. Courvalin, *Microb. Drug Resist.* 2, 219 (1996).
11. J. C. Silva, A. Haldimann, M. K. Prahalad, C. T. Walsh, B. L. Wanner, *Proc. Natl. Acad. Sci. U.S.A.* 95 11951 (1998).
12. M. Arthur, C. Molinas, S. Dutka-Malen, P. Courvalin, *Gene* 103, 133 (1991).
13. G. D. Wright, C. Molinas, M. Arthur, P. Courvalin, C. T. Walsh, *Antimicrob. Agents. Chemother.* 7, 1514 (1992).
14. T. D. Bugg et al., *Biochem.* 30, 10408 (1991).
15. Z. Wu, C. T. Walsh, *Proc. Natl. Acad. Sci. U.S.A.* 92, 11603 (1995).
16. P. E. Reynolds, F. Depardieu, S. Dutka-Malen, M. Arthur, P. Courvalin, *Mol. Microbiol.* 6, 1065 (1994).
17. R. Xu, G. Greiveldinger, L. E Marenus, *J. Am. Chem. Soc.* 121, 4898 (1999).
18. M. Ge et al., *Science* 284, 507 (1999).
19. U. N. Sundram, J. H. Griffin, T. I. Nicas, *J. Am. Chem. Soc.* 118, 13107 (1996).
20. M. H. J. Ohlmeyer et al., *Proc. Natl. Acad. Sci. U.S.A.* 90, 10922 (1993).
21. H. P. Nestler, P. A. Bartlett, W. C. Still, *J. Org. Chem.* 59, 4723 (1994).
22. S. Handwerger, M. J. Pucci, A. Kolokathis, *Antimicrob. Agents. Chemother.* 34, 358 (1990).
23. A. E. Jacob, S. J. Hobbs, *J. Bacteriol.* 117, 360 (1974).
24. Templin, M. F., Ursinus, A., and Holtje, J. V. (1999) A defect in cell wall recycling triggers autolysis during the stationary growth phase of *Escherichia coli*. *EMBO J.*, 18, 4108–17.
25. A. T. Ulijasz, A. Grenaderand, B. Weisblum, *J. Bacteriol.* 178, 6305 (1996).
26. M. H. Lai, D. R. Kirsch, *Antimicrob. Agents Chemother.* 40, 1645 (1996).
27. M. Baptista, F. Depardieu, P. Courvalinand, M. Arthur, *Antimicrob. Agents Chemother.* 40, 2291 (1996).
28. Li, G., Ph.D. Thesis, Columbia University (1993).
29. Chen, Y., Suenaga, T., Still, W. C. *J. Am. Chem. Soc.* 118, 1813 (1996).
30. Burger, M., Still, W. C., *J. Org. Chem.*, 60, 7382 (1995).
31. Borchardt, A., Still, W. C., *J. Am. Chem. Soc.* 116, 373 (1994).
32. Wenemers, H., Ph.D. Thesis, Columbia University (1996).
33. Iorio, E. J., Ph.D. Thesis, Columbia University (1999).
34. Nelson, R. R. 1999, "Intrinsically Vancomycin Resistant Gram-positive Organisms: Clinical Relevance and Implications for Infection Control." *Journal of Hospital Infection*, 42: 275–282.

What is claimed is:

1. A method of treating a subject afflicted with an infection caused by vancomycin resistant Gram-positive bacteria in which, resistance results from the conversion of an amide bond to an ester bond in the cell wall peptide precursors of the bacteria which comprises administering to the subject an antibacterial amount of vancomycin or a homolog of vancomycin and an amount of an agent effective to selectively cleave said ester bond so as to thereby treat the subject.

2. The method of claim 1, wherein the subject is a human being.

3. The method of claim 1, wherein the agent is an activated nucleophile, is not a peptide, and is further characterized by the presence within the agent of an electrophile and chirality complementary to a bacterial cell wall peptide.

4. The method of claim 1, where the agent catalytically cleaves said ester bond.

5. The method of claim 1, wherein said ester bond is present in the structure D—Ala—D—Lac.

6. The method of claim 1, wherein the agent is administered prior to administering vancomycin or the homolog of vancomycin.

7. The method of claim 4, wherein the agent is administered a sufficient period of time prior to administering vancomycin or the homolog of vancomycin to permit cleavage of said ester bond to be effected.

8. The method of claim 1, wherein the agent and vancomycin or the homolog of vancomycin are administered simultaneously.

9. The method of claim 8, wherein the agent is covalently attached to vancomycin or the homolog of vancomycin.

10. The method of claim 1, wherein the bacteria are Van A, Van B, Van D or Van G Gram positive bacteria.

11. The method of claim 1, wherein the bacteria are Staphylococcus bacteria.

12. The method of claim 10, wherein the bacteria are *S. aureus* bacteria.

13. The method of claim 1, wherein the bacteria are Enterococcus bacteria.

14. The method of claim 1, wherein the bacteria are Streptococcus bacteria.

15. The method of claim 1, wherein the bacteria are Leuconostoc bacteria.

16. The method of claim 1, wherein the bacteria are Pediococcus bacteria.

17. The method of claim 1, wherein the bacteria are Lactobacillus bacteria.

18. The method of claim 1, wherein the bacteria are Erysipelothrix bacteria.

19. A method of killing vancomycin resistant Van A, Van B, Van D, or Van G Gram-positive bacteria which comprises contacting the bacteria with an agent that selectively cleaves D—Ala—D—Lac cell wall depsipeptide in the bacteria in an amount effective to cleave such depsipeptide and an antibacterial amount of vancomycin or a homolog of vancomycin so as to thereby kill the bacteria.

20. The method of claim 19, wherein the agent is an activated nucleophile, is not a peptide, and is further characterized by the presence within the agent of an electrophile and chirality complementary to a bacterial cell wall depsipeptide.

21. The method of claim 19, where the agent catalytically cleaves said D—Ala—D—Lac cell wall depsipeptide.

22. The method of claim 19, wherein the agent is administered prior to administering vancomycin or the homolog of vancomycin.

23. The method of claim 22, wherein the agent is administered a sufficient period of time prior to administering vancomycin or the homolog of vancomycin to permit cleavage of the D—Ala—D—Lac cell wall depsipeptide to be effected.

24. The method of claim 19, wherein the agent and vancomycin or the homolog of vancomycin are administered simultaneously.

25. The method of claim 24, wherein the agent is covalently attached to vancomycin or the homolog of vancomycin.

26. The method of claim 19, wherein the bacteria are Staphylocoecus bacteria.

27. The method of claim 26, wherein the bacteria are S. aureus bacteria.

28. The method of claim 19, wherein the bacteria are Enterococcus bacteria.

29. The method of claim 19, wherein the bacteria are Streptococcus bacteria.

30. A method of treating a subject afflicted with an infection caused by glycopeptide antibiotic resistant Gram-positive bacteria in which resistance results from the conversion of an amide bond to an ester bond in the cell wall peptide precursors of the bacteria which comprises administering to the subject an antibacterial amount of a glycopeptide antibiotic and an amount of an agent effective to selectively cleave said ester bond so as to thereby treat the subject.

31. A method of killing glycopeptide antibiotic resistant Gram-positive bacteria which comprises contacting the bacteria with an agent that selectively cleaves D—Ala—D—Lac cell wall depsipeptide in the bacteria in an amount effective to cleave such depsipeptide and an antibacterial amount of the glycopeptide antibiotic so as to thereby kill the bacteria.

32. The method of claim 31, wherein the bacteria are Staphylococcus bacteria.

33. The method of claim 31, wherein the bacteria are S. aureus bacteria.

34. The method of claim 31, wherein the bacteria are Enterococcus bacteria.

35. The method of claim 31, wherein the bacteria are Streptococcus bacteria.

36. The method of claim 31, wherein the bacteria are Leuconostoc bacteria.

37. The method of claim 31, wherein the bacteria are Pediococcus bacteria.

38. The method of claim 31, wherein the bacteria are Lactobacillus bacteria.

39. The method of claim 31, wherein the bacteria are Erysipelothrix bacteria.

40. The method of claim 19, wherein the bacteria are Leuconostoc bacteria.

41. The method of claim 19, wherein the bacteria are Pediococcus bacteria.

42. The method of claim 19, wherein the bacteria are Lactobacillus bacteria.

43. The method of claim 19, wherein the bacteria are Erysipelothrix bacteria.

44. The method of claim 30, wherein the subject is a human being.

45. The method of claim 30, wherein the agent is an activated nucleophile, is not a peptide, and is further characterized by the presence within the agent of an electrophile and chirality complementary to a bacterial cell wall peptide.

46. The method of claim 30, wherein the agent has the structure:

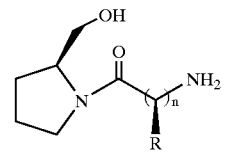

wherein n is an integer from 1 to 6 inclusive and R is hydrogen or a $C_1$ to $C_6$ straight chain or branched alkyl group.

47. The method of claim 30, where the agent catalytically cleaves said ester bond.

48. The method of claim 30, wherein said ester bond is present in the structure D—Ala—D—Lac.

49. The method of claim 30, wherein the agent is administered prior to administering the glycopeptide antibiotic.

50. The method of claim 49, wherein the agent is administered a sufficient period of time prior to administering the glycopeptide antibiotic to permit cleavage of said ester bond to be effected.

51. The method of claim 30, wherein the agent and the glycopeptide antibiotic are administered simultaneously.

52. The method of claim 51, wherein the agent is covalently attached to the glycopeptide antibiotic.

53. The method of claim 30, wherein the bacteria are Staphylococcus bacteria.

54. The method of claim 53, wherein the bacteria are S. aureus bacteria.

55. The method of claim 30, wherein the bacteria are Enterococcus bacteria.

56. The method of claim 30, wherein the bacteria are Streptococcus bacteria.

57. The method of claim 30, wherein the bacteria are Leuconostoc bacteria.

58. The method of claim 30, wherein the bacteria are Pediococcus bacteria.

59. The method of claim 30, wherein the bacteria are Lactobacillus bacteria.

60. The method of claim 30, wherein the bacteria are Erysipelothrix bacteria.

61. The method of claim 31, wherein the agent is an activated nucleophile, is not a peptide, and is further characterized by the presence within the agent of an electrophile and chirality complementary to a bacterial cell wall depsipeptide.

62. The method of claim 31, wherein the agent has the structure:

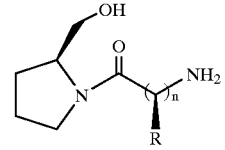

wherein n is an integer from 1 to 6 inclusive and R is hydrogen or a $C_1$ to $C_6$ straight chain or branched alkyl group.

63. The method of claim 31, where the agent catalytically cleaves the D—Ala—D—Lac cell wall depsipeptide.

64. The method of claim 31, wherein the agent is administered prior to administering the glycopeptide antibiotic.

65. The method of claim 31, wherein the agent is administered a sufficient period of time prior to administering the glycopeptide antibiotic to permit cleavage of the D—Ala—D—Lac depsipeptide to be effected.

66. The method of claim 31, wherein the agent and the glycopeptide antibiotic are administered simultaneously.

67. The method of claim 66, wherein the agent is covalently attached to the glycopeptide antibiotic.

68. The method of claim 1, wherein the agent has the structure:

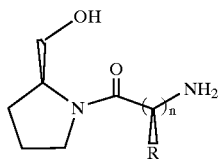

wherein n is an integer from 1 to 6 inclusive and R is hydrogen or a $C_1$ to $C_6$ straight chain or branched alkyl group.

69. The method of claim 19, wherein the agent has the structure:

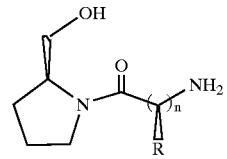

wherein n is an integer from 1 to 6 inclusive and R is hydrogen or a $C_1$ to $C_6$ straight chain or branched alkyl group.

70. The method of claim 46, wherein n=5 and R=H.
71. The method of claim 62, wherein n=5 and R=H.
72. The method of claim 68, wherein n=5 and R=H.
73. The method of claim 69, wherein n=5 and R=H.

\* \* \* \* \*